(12) United States Patent
Hashimoto et al.

(10) Patent No.: US 7,067,546 B2
(45) Date of Patent: Jun. 27, 2006

(54) CRYSTAL AND PROCESS FOR PRODUCING THE SAME

(75) Inventors: Hideo Hashimoto, Atlanta, GA (US); Hideaki Maruyama, Suita (JP)

(73) Assignee: Takeda Pharmaceutical Company, Osaka (JP)

( * ) Notice: Subject to any disclaimer, the term of this patent is extended or adjusted under 35 U.S.C. 154(b) by 26 days.

(21) Appl. No.: 10/485,593

(22) PCT Filed: Aug. 1, 2002

(86) PCT No.: PCT/JP02/07861

§ 371 (c)(1), (2), (4) Date: Feb. 2, 2004

(87) PCT Pub. No.: WO03/014112

PCT Pub. Date: Feb. 20, 2003

(65) Prior Publication Data

US 2004/0215023 A1   Oct. 28, 2004

(30) Foreign Application Priority Data

Aug. 3, 2001   (JP) .............................. 2001-236802

(51) Int. Cl.
  *A61K 31/41*   (2006.01)
  *C07C 255/00*   (2006.01)
  *C07D 257/00*   (2006.01)

(52) U.S. Cl. ...................... 514/381; 548/252; 548/253; 558/414

(58) Field of Classification Search ................ 514/381; 548/253, 252; 558/414
See application file for complete search history.

(56) References Cited

U.S. PATENT DOCUMENTS 5,196,444 A * 3/1993 Naka et al. .................. 514/381
6,177,587 B1 * 1/2001 Hashimoto et al. ......... 558/414

OTHER PUBLICATIONS

John McMurray, Organic Chemistry, 1988, Brooks/Cole Publishing Company, $2^{nd}$ Ediction, p. 355.*

Kubo et al., "Nonpeptide Angiotensin II Receptor Antagonists. Synthesis and Biological Activity of Benzimidazolecarboxylic Acids" J. Med. chem. 36(15):2182-2195(1993).

Matsunaga, et al. "Solid-State Characterization of Candesartan Cilexetil (TCV-116): Crystal Structure and Moleuclar Mobility:" Chem. Pharm. Bull. 47(2) 182-186 (1999).

* cited by examiner

*Primary Examiner*—Kamal A. Saeed
*Assistant Examiner*—Susannah L. Chung
(74) *Attorney, Agent, or Firm*—Mark Chao; Elaine M. Ramesh

(57) ABSTRACT

A process for producing crystals of 2-ethoxy-1-[[2'-(1H-tetrazol-5-yl) biphenyl-4-yl]methyl]-1H-benzimdazole-7-carboxylic acid (compound (I)), characterized by dissolving or suspending the compound (I) or a salt thereof in a solvent comprising an aprotic polar solvent and crystallizing it. By the process, the contaminants which are contained in the compound (I) or its salt and are difficult to remove, such as tin compounds, analogues of the compound (I), and a residual organic solvent, can be easily removed. Crystals of the compound (I) can be efficiently and easily mass-produced in high yield on an industrial scale.

10 Claims, No Drawings

CRYSTAL AND PROCESS FOR PRODUCING THE SAME

This application is the National Phase filing of International Patent Application No. PCT/JP02/07861, filed Aug. 1, 2002.

TECHNICAL FIELD

The present invention relates to a process for producing a crystal of 2-ethoxy-1-[[2'-(1H-tetrazol-5-yl)biphenyl-4-yl]methyl]-1H-benzimdazole-7-carboxylic acid (hereinafter, abbreviated as Compound (I) in some cases) which contains 5000 ppm or less of tetrahydrofuran, do not substantially contain contaminants such as a tin compound, analogues (e.g. ketone compound, ethyl ester compound) of 2-ethoxy-1-[[2'-(1H-tetrazol-5-yl)biphenyl-4-yl]methyl]-1H-benzimidazole-7-carboxylic acid and a residual organic solvent (e.g. dichloromethane), and is pyrogen-free and sterile, a crystal obtained by the process and a pharmaceutical composition containing the crystal.

BACKGROUND ART

A process for producing Compound (I) having the depressor activity or a salt thereof is described, for example, in EP-A-0881212 and EP-A-0459136. However, since Compound (I) is synthesized using an organotin compound, the organotin compound which is difficult to remove remains in the compound. In the process described in EP-A-0881212 and EP-A-0459136, about 2000 ppm (measured by atomic absorption) of a tin compound is contained in Compound (I).

In addition, since the analogues such as 2,3-dihydro-2-oxo-1-[[2'-(1H-tetrazol-5-yl)biphenyl-4-yl]methyl]-1H-benzimidazole-7-carboxylic acid [hereinafter, referred to as ketone compound in some cases] and ethyl 2-ethoxy-1-[[2'-(1H-tetrazol-5-yl)biphenyl-4-yl]methyl]-1H-benzimdazole-7-carboxylate [hereinafter, referred to as ethyl ester compound in some cases] have the similar properties to those of Compound (I), it is difficult to remove those analogues, and considerable amounts of them (total: about 3%) are contained in Compound (I). In addition, Compound (I) has the very low solubities in various solvents, this is one of factors making purification of Compound (I) difficult and, for this reason, a mixed solvent of dichloromethane-methanol in which Compound (I) is relatively highly soluble has been previously used in purification. As a result, highly toxic dichloromethane remains in Compound (I) at a few hundreds ppm.

Like this, considerable amounts of a tin compound, analogues and dichloromethane are present in Compound (I) which has been prepared by the conventional process. However, previously, since a preparation product containing Compound (I) as an original drug is not used as a medicament, Compound (I) is derived to (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate [hereinafter, referred to as candesartan cilexetil in some cases] via a number of steps, and a preparation product containing the same compound as an original drug is used as a medicament, the contaminants such as a tin compound, a ketone compound, an ethyl ester compound and dichloromethane are removed via a number of steps, and the presence of these contaminants in Compound (I) was not problematic at all. However, when a preparation product containing Compound (I) as an original drug is developed as a medicament (e.g. injectable), the presence of a tin compound, analogues and dichloromethane at an amount exceeding a tolerable amount becomes a serious problem.

In the conventional process, in order to remove contaminants such as a tin compound, analogues and the like, purification was carried out using a mixed solvent of dichloromethane-methanol. However, for developing a preparation product as a medicament containing Compound (I) as an original drug, the purification efficacy of the conventional process is not sufficient, and a few thousands ppm of a tin compound and a few % of analogues remain even after purification. In addition, since dichloromethane is used as a purification solvent, a few hundreds ppm of dichloromethane remains in Compound (I). Because of the presence of such the tin compound, analogues and dichloromethane at amounts exceeding tolerable amounts, it has previously been difficult to develop a preparation product as a medicament containing compound (I) as an original drug. For this reason, there is desired a process which can afford Compound (I) containing small residual amounts of a tin compound, analogues and dichloromethane which can be employed as a medicament.

DISCLOSURE OF THE INVENTION

The present inventors extensively studied a process for producing a crystal of Compound (I), and first found that, when Compound (I) or a salt thereof is dissolved or suspended in a solvent containing an aprotic polar solvent to crystallize, unexpectedly, contaminants such as a tin compound, analogues (e.g. ketone compound, ethyl ester compound) of Compound (I) and a residual organic solvent (e.g. dichloromethane) which are usually difficult to remove, can be easily removed, and this process is a process which is sufficiently satisfactory on an industrial scale and, based on these findings, the present invention was completed.

That is, the present invention relates to:

(1) a process for producing a crystal of 2-ethoxy-1-[[2'-(1H-tetrazol-5-yl)biphenyl-4-yl]methyl]-1H-benzimidazole-7-carboxylic acid, which comprises dissolving or suspending 2-ethoxy-1-[[2'-(1H-tetrazol-5-yl)biphenyl-4-yl]methyl]-1H-benzimidazole-7-carboxylic acid or a salt thereof in a solvent containing an aprotic polar solvent, and crystallizing it, (2) a process for producing a crystal of 2-ethoxy-1-[[2'-(1H-tetrazol-5-yl)biphenyl-4-yl]methyl]-1H-benzimidazole-7-carboxylic acid, which comprises crystallizing from a solution or suspension containing 2-ethoxy-1-[[2'-(1H-tetrazol-5-yl)biphenyl-4-yl]methyl]-1H-benzimidazole-7-carboxylic acid or a salt thereof and an aprotic polar solvent, (2') a process for producing a crystal of 2-ethoxy-1-[[2'-(1H-tetrazol-5-yl)biphenyl-4-yl]methyl]-1H-benzimidazole-7-carboxylic acid, which comprises crystallizing from a solution containing 2-ethoxy-1-[[2'-(1H-tetrazol-5-yl)biphenyl-4-yl]methyl]-1H-benzimidazole-7-carboxylic acid and an aprotic polar solvent, (3) a process for producing a crystal of 2-ethoxy-1-[[2'-(1H-tetrazol-5-yl)biphenyl-4-yl]methyl]-1H-benzimidazole-7-carboxylic acid, which comprises dissolving or suspending 2-ethoxy-1-[[2'-(1H-tetrazol-5-yl)biphenyl-4-yl]methyl]-1H-benzimidazole-7-carboxylic acid or a slat thereof in a solvent containing an aprotic polar solvent, followed by mixing the solution or suspension with water and/or an organic solvent to crystallize, (4) the process according to the above-mentioned (3), wherein the solvent containing an aprotic polar solvent is a mixed solvent containing an aprotic polar solvent and water, (5) the process according to the above-mentioned (3), wherein the solvent containing an aprotic polar solvent is a mixed solvent containing an aprotic polar solvent and an organic solvent, (6) the process according to the above-mentioned (3), wherein the solvent containing an aprotic polar solvent is a mixed solvent containing an aprotic polar solvent, water and an organic solvent, (7) the process according to the above-mentioned (3), wherein 2-ethoxy-1-[[2'-(1H-tetrazol-5-yl)biphenyl-4-yl]methyl]-1H-benzimidazole-7-carboxylic acid or a salt thereof is dissolved or suspended in a solvent containing an aprotic polar solvent, followed by mixing the solution or suspension with an organic solvent to crystallize, (8) the process according to the above-mentioned (3), wherein 2-ethoxy-1-[[2'-(1H-tetrazol-5-yl)biphenyl-4-yl]methyl]-1H-benzimidazole-7-carboxylic acid or a salt thereof is dissolved or suspended in a solvent containing an aprotic polar solvent, followed by mixing the solution or suspension with water and an organic solvent to crystallize, (9) the process according to the above-mentioned (1), (2), (2') or (3), wherein the aprotic polar solvent is one or more kinds of solvents selected from tetrahydrofuran, dimethylformamide, dimethyl sulfoxide and hexamethylphosphoric triamide,

(10) the process according to the above-mentioned (1), (2), (2') or (3), wherein the aprotic polar solvent is tetrahydrofuran,

(11) the process according to the above-mentioned (1), (2), (2') or (3), comprising crystallizing at about 0 to about 30° C.,

(12) the process according to the above-mentioned (3), wherein the organic solvent is a solvent described in a class 2 or 3 of guideline of International Conference on Harmonisation of Pharmaceutical for Human USE (ICH),

(13) the process according to the above-mentioned (12), wherein the solvent described in a class 2 or 3 of ICH guideline is one or more kinds of organic solvents selected from ketones, acetic acid esters, alcohols, ethers and hydrocarbons,

(14) the process according to the above-mentioned (12), wherein the solvent described in a class 2 or 3 of ICH guideline is one or more kinds of organic solvents selected from acetone, ethyl acetate, methanol, ethanol, propanol, tert-butyl methyl ether, hexane and heptane,

(15) the process according to the above-mentioned (5), wherein the organic solvent is a ketone or an alcohol,

(16) the process according to the above-mentioned (5), wherein the organic solvent is acetone or ethanol,

(17) the process according to the above-mentioned (3), wherein mixing with water and/or an organic solvent includes a step of adding water and/or an organic solvent dropwise to a solution or suspension in which 2-ethoxy-1-[[2'-(1H-tetrazol-5-yl)biphenyl-4-yl]methyl]-1H-benzimidazole-7-carboxylic acid or a salt thereof is dissolved or suspended in a solvent containing an aprotic polar solvent,

(18) the process according to the above-mentioned (3), wherein mixing with water and/or an organic solvent includes a step of adding dropwise a solution or suspension in which 2-ethoxy-1-[[2'-(1H-tetrazol-5-yl)biphenyl-4-yl]methyl]-1H-benzimidazole-7-carboxylic acid or a slat thereof is dissolved or suspended in a solvent containing an aprotic polar solvent, to water and/or an organic solvent,

(19) the process according to the above-mentioned (3), wherein the organic solvent is composed of two or more organic solvents,

(20) the process according to the above-mentioned (3), wherein mixing with an organic solvent includes a step of (a) mixing with one or more organic solvents (B1) selected from acetone, ethyl acetate, methanol, ethanol and propanol and, thereafter, (b) mixing with an organic solvent (B2) selected from heptane, hexane and tert-butyl methyl ether,

(21) the process according to the above-mentioned (3), wherein the amount of the organic solvent is 1 to 10-fold (volume) of an aprotic polar solvent,

(22) the process according to the above-mentioned (3), wherein the amount of water is 0.1 to 3-fold (volume) of an aprotic polar solvent,

(23) the process according to the above-mentioned (3), wherein the mixing volume ratio of water and an organic solvent is 1:50 to 5:1,

(24) the process according to the above-mentioned (4), wherein the mixing volume ratio of an aprotic polar solvent and water is 20:1 to 5:1,

(25) the process according to the above-mentioned (5), wherein the mixing volume ratio of an aprotic polar solvent and an organic solvent is 20:1 to 5:1,

(26) the process according to the above-mentioned (6), wherein the mixing volume ratio of an aprotic polar solvent/ an organic solvent/ water is 2 to 10/2 to 10/1,

(27) the process according to the above-mentioned (1), (2), (2') or (3), wherein a step in which the crystallized crystal is dissolved or suspended in a solvent containing an aprotic polar solvent, followed by being crystallized, is repeated one or more times,

(28) the process according to the above-mentioned (1), (2), (2') or (3), which further comprises a step of removing pyrogens and/or a sterilizing step,

(29) the process according to the above-mentioned (1), (2), (2') or (3), wherein the crystallized crystal is substantially pyrogen-free,

(30) the process according to the above-mentioned (1), (2), (2') or (3), wherein the crystallized crystal is substantially sterile,

(31) a process for producing a crystal of 2-ethoxy-1-[[2'-(1H-tetrazol-5-yl)biphenyl-4-yl]methyl]-1H-benzimidazole-7-carboxylic acid, which comprises reacting methyl 1-[(2'-cyanobiphenyl-4-yl)methyl]-2-ethoxybenzimidazole-7-carboxylate or a salt thereof with a compound represented by the formula $(R)_3SnN_3$ (wherein R represents alkyl having a carbon number of 4 to 18), and subjecting the resulting methyl 2-ethoxy-1-[[2'-(1H-tetrazol-5-yl)biphenyl-4-yl]methyl]benzimidazole-7-carboxylate or a salt thereof to a hydrolysis reaction, followed by dissolving or suspending the resulting 2-ethoxy-1-[[2'-(1H-tetrazol-5-yl)biphenyl-4-yl]methyl]-1H-benzimidazole-7-carboxylic acid or a salt thereof in a solvent containing an aprotic polar solvent to crystallize,

(32) the process according to the above-mentioned (31), wherein the crystal does not substantially contain a tin compound,

(33) the process according to the above-mentioned (31), wherein the content of a tin compound in the crystal is 1000 ppm or less,

(34) the process according to the above-mentioned (31), wherein the content of a tin compound in the crystal is 10 ppm or less,

(35) the process according to the above-mentioned (31), wherein the crystal does not substantially contain an analogue of 2-ethoxy-1-[[2'-(1H-tetrazol-5-yl)biphenyl-4-yl]methyl]-1H-benzimidazole-7-carboxylic acid,

(36) the process according to the above-mentioned (31), wherein the content of an analogue of 2-ethoxy-1-[[2'-(1H- tetrazol-5-yl)biphenyl-4-yl]methyl]-1H-benzimidazole-7-carboxylic acid in the crystal is 1% or less,

(37) the process according to the above-mentioned (31), wherein the crystal does not substantially contain residual organic solvent,

(38) the process according to the above-mentioned (31), wherein the content of all residual organic solvents in the crystal is 5000 ppm or less, and an amount of residual dichloromethane is less than 50 ppm,

(39) a crystal of 2-ethoxy-1-[[2'-(1H-tetrazol-5-yl)biphenyl-4-yl]methyl]-1H-benzimidazole-7-carboxylic acid obtained by reacting methyl 1-[(2'-cyanobiphenyl-4-yl)methyl]-2-ethoxybenzimidazole-7-carboxylate or a salt thereof with a compound represented by the formula $(R)_3SnN_3$ (wherein R represents alkyl having a carbon number of 4 to 18), and subjecting the resulting methyl 2-ethoxy-1-[[2'-(1H-tetrazol-5-yl)biphenyl-4-yl]methyl]benzimidazole-7-carboxylate or a salt thereof to a hydrolysis reaction, followed by dissolving or suspending the resulting 2-ethoxy-1-[[2'-(1H-tetrazol-5-yl)biphenyl-4-yl]methyl]-1H-benzimidazole-7-carboxylic acid or a salt thereof in a solvent containing an aprotic polar solvent to crystallize,

(40) a crystal of 2-ethoxy-1-[[2'-(1H-tetrazol-5-yl)biphenyl-4-yl]methyl]-1H-benzimidazole-7-carboxylic acid containing 5000 ppm or less of tetrahydrofuran, (40') the crystal according to the above-mentioned (39), which contains 5000 ppm or less of tetrahydrofuran,

(41) the crystal according to the above-mentioned (39) or (40), which does not substantially contain a tin compound,

(42) the crystal according to the above-mentioned (39) or (40), wherein the content of a tin compound is 1000 ppm or less,

(43) the crystal according to the above-mentioned (39) or (40), wherein the content of a tin compound is 10 ppm or less,

(44) the crystal according to the above-mentioned (39) or (40), which does not substantially contain an analogue of 2-ethoxy-1-[[2'-(1H-tetrazol-5-yl)biphenyl-4-yl]methyl]-1H-benzimidazole-7-carboxylic acid,

(45) the crystal according to the above-mentioned (39) or (40), wherein the content of an analogue of 2-ethoxy-1-[[2'-(1H-tetrazol-5-yl)biphenyl-4-yl]methyl]-1H-benzimidazole-7-carboxylic acid is 1% or less,

(46) the crystal according to the above-mentioned (39) or (40), which does not substantially contain residual organic solvent,

(47) the crystal according to the above-mentioned (39) or (40), wherein the content of all residual organic solvents is 5000 ppm or less, and an amount of residual dichloromethane is less than 50 ppm,

(48) the crystal according to the above-mentioned (39) or (40), which is substantially pyrogen-free,

(49) the crystal according to the above-mentioned (39) or (40), which is substantially sterile, and

(50) a pharmaceutical composition containing the crystal according to the above-mentioned (39) or (40).

As described above, the present invention provides a process for producing a crystal of Compound (I), which comprises crystallizing from a solution or suspension (preferably solution) containing Compound (I) or a salt thereof and an aprotic polar solvent.

Specifically, a crystal of Compound (I) can be produced by dissolving or suspending (preferably dissolving) Compound (I) or a salt thereof in a solvent containing an aprotic polar solvent, and crystallizing it. (herein, "an aprotic polar solvent" used for dissolving or suspending Compound (I) or a salt thereof is referred to as an "aprotic polar solvent (A)" in some cases.)

That is, a crystal of Compound (I) can be produced by dissolving or suspending Compound (I) or a salt thereof in a solvent containing the aprotic polar solvent (A), to obtain "a solution or suspension containing Compound (I) or a salt thereof and the aprotic polar solvent (A)", and crystallizing from the solution or suspension.

More specifically, for example, a crystal of Compound (I) or a salt thereof can be produced by dissolving or suspending Compound (I) or a salt thereof in a solvent containing the aprotic polar solvent (A) and, thereafter, mixing the solution or suspension with water and/or an organic solvent, and crystallizing it. (Herein, "water" which is used by mixing with the solution or suspension for the purpose of crystallizing Compound (I) from "a solution or suspension containing Compound (I) or a salt thereof and the aprotic polar solvent (A)" is referred to as "water (W2)", and the "organic solvent" is referred to as an "organic solvent (B)" in some cases.)

Compound (I) in the process of the present invention is a compound (general name: Candesartan) represented by:

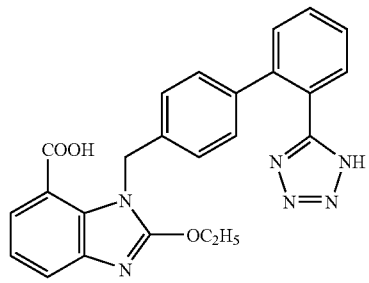

The compound (raw material) which is subjected to the process of the present invention may be itself or a pharmacologically acceptable salt. Examples of such salt include salts with inorganic bases (e.g. alkali metal such as sodium, potassium etc., alkaline earth metal such as calcium, magnesium etc., transition metal such as zinc, iron, copper etc.) or organic bases (e.g. organic amines such as trimethylamine, triethylamine, pyridine, picoline, ethanolamine, diethanolamine, triethanolamine, dicyclohexylamine, N,N'-dibenzylethylenediamine, basic amino acids such as arginine, lysine, ornithine etc.), salts with an inorganic acids or organic acids (e.g. hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric, maleic acid, citric acid, succinic acid, malic acid, methanesulfonic acid, benzensulfonic acid, p-toluenesulfonic acid etc.), and salts with acidic amino acids such as aspartic acid, glutamic acid, and the like.

For example, a crystal of Compound (I) • 2Na can be synthesized by the following process: By dissolving Compound (I) and 2 equivalent of a Na source (e.g. sodium hydroxide, sodium methoxide, sodium ethoxide, sodium hydride etc.) in water or an organic solvent (any organic solvent may be used as far as it dissolves Compound (I) and a Na source, and examples thereof include methanol, ethanol, acetonitrile etc.) or a water-organic solvent mixed solvent, concentrating the solution, and adding a solvent (e.g. acetone-water mixed solvent, ethanol-water mixed solvent, methanol-water, acetonitrile-water mixed solvent etc.), a crystal of Compound (I) • 2Na salt can be synthesized (Elemental Analysis: Anal Calc. For $C_{24}H_{18}N_6Na_2O_3$: C, 59.51; H, 3.75; N, 17.35; Found: C, 59.50; H, 3.77; N, 17.23). (Atomic Absorption (Na): Calc. 9.49%, Obs. 9.5%).

For example, amorphous of Compound (I) • 2Na can be synthesized by the following process: By dissolving Compound (I) and 2 equivalent of a Na source (e.g. sodium hydroxide, sodium methoxide, sodium ethoxide, sodium hydride etc.) in water or an organic solvent (any organic solvent may be used as far as it dissolves Compound (I) and a Na source, and examples thereof include acetonitrile, methanol, ethanol etc.) or a water-organic solvent mixed solvent, concentrating the solution to distill the organic solvent off, and lyophilizing it, an amorphous of Compound (I) • 2Na salt can be synthesized.

Compound (I) or a salt thereof which is subjected to the process for producing a crystal of the present invention can be prepared according to the process described, for example, in EP-A-0881212 and EP-A 0459136 or a similar process.

The "solution or suspension (preferably solution) containing Compound (I) or a salt thereof and the aprotic polar solvent (A)" can be prepared by dissolving or suspending (preferably dissolving) Compound (I) prepared by the aforementioned known per se process or a salt thereof in a solvent containing the aprotic polar solvent (A).

Specifically, methyl 1-[(2'-cyanobiphenyl-4-yl)methyl]-2-ethoxybenzimidazole-7-carboxylate (hereinafter, abbreviated as BEC in some cases) or a salt thereof and a compound represented by the formula $(R)_3SnN_3$ [wherein R represents alkyl having a carbon number of 4 to 18 (preferably, alkyl having a carbon number of 7 to 18; more preferably, octyl)] are reacted, the resulting methyl 2-ethoxy-1-[[2"-(1H-tetrazol-5-yl)biphenyl-4-yl]methyl]benzimidazole-7-carboxylate (hereinafter, abbreviated as MET in some cases) or a salt thereof is subjected to a hydrolysis reaction, and the resulting Compound (I) or a salt thereof is dissolved or suspended in a solvent containing the aprotic polar solvent (A), whereby, "a solution or suspension containing Compound (I) or a salt thereof and the aprotic polar solvent (A)" (hereinafter, simply referred to as "a solution or suspension containing Compound (I) or a salt thereof" in some cases) can be obtained.

Examples of the salt of BEC or MET include the same salts as those of Compound (I) mentioned above.

Herein, a process for reacting BEC or a salt thereof with a compound represented by the formula $(R)_3SnN_3$ (wherein R represents alkyl having a carbon number of 4 to 18) to prepare MET or a salt thereof can be carried out according to the process described, for example, in EP-A 0578125. A hydrolysis reaction of MET or a salt thereof can be carried out, for example, by mixing the resulting MET or a salt thereof with, preferably, an aqueous alkali solution such as an alkali metal hydroxide or an alkali metal alkoxide. Examples of the alkali metal hydroxide include sodium hydroxide and potassium hydroxide. Examples of the alkali metal alkoxide include sodium methoxide, sodium ethoxide, potassium methoxide and potassium ethoxide. An amount of the alkali to be used in a hydrolysis reaction is about 2 to 5 equivalent relative to MET or a salt thereof. The hydrolysis reaction is carried out at a temperature of about 40 to about 100° C., preferably about 50 to about 80 ° C. under stirring. A reaction time is about 0.5 to about 10 hours, preferably about 1 to about 5 hours.

Compound (I) or a salt thereof used in preparing the above solution or suspension may be any of a solid (crystalline, amorphous) and an oil, may be any of a hydrate or a non-hydrate, and may not be isolated or purified.

The aprotic polar solvent (A) may be any solvent as far as it is an aprotic polar solvent, and examples thereof include THF (tetrahydrofuran), DMF (dimethylformamide), DMSO (dimethyl sulfoxide), and HMPA (hexamethylphosphoric triamide) and a mixed solvent of two or more (preferably two to three) of them.

Inter alia, THF, DMF and DMSO are preferable, and THF is particularly preferred.

The "solvent containing the aprotic polar solvent (A)" may further contain an organic solvent and/or water in addition to the aprotic polar solvent (A). (Herein, the "organic solvent" which is a solvent used by mixing with the aprotic polar solvent (A) for the purpose of dissolving or suspending Compound (I) or a salt thereof is referred to as an "organic solvent (C)", and "water" is referred to as "water (W1)" in some cases.)

As the organic solvent (C), ketones or alcohols are preferable.

Examples of the ketones include acetone, methyl ethyl ketone, methyl isopropyl ketone, methyl butyl ketone and methyl isobutyl ketone.

Examples of the alcohols include lower alcohols such as methanol, ethanol, 1-propanol, 2-propanol, 1-butanol, 2-butanol, 2-methyl-1-propanol, pentanol and 3-methyl-1-butanol; lower alcohols substituted with $C_{1-3}$alkoxy such as 2-methoxyethanol and 2-ethoxyethanol; ethylene glycol.

As the organic solvent (C), acetone or ethanol is particularly preferred.

As the solvent used for the purpose of dissolving or suspending Compound (I) or a salt thereof, that is, the "solvent containing the aprotic polar solvent (A)", (1) THF, (2) DMSO, (3) a mixed solvent of THF and water, (4) a mixed solvent of THF, acetone and water, (5) a mixed solvent of THF, ethanol and water, and (6) a mixed solvent of DMSO and acetone are preferred. (1) THF and (2) a mixed solvent of THF and water are particularly preferred.

When the aprotic polar solvent (A) and water (W1) are used upon preparation of "a solution or suspension containing Compound (I) or a salt thereof and the aprotic polar solvent (A)", it is preferable that a mixing volume ratio (aprotic polar solvent (A): water (W1)) is 20:1 to 5:1 (preferably 12:1 to 7:1).

When the aprotic polar solvent (A) and the organic solvent (C) are used upon preparation of "a solution or suspension containing Compound (I) or a salt thereof and the aprotic polar solvent (A)", it is preferable that a mixing volume ratio (aprotic polar solvent (A): organic solvent (C)) is 20:1 to 1:2 (preferably 10:1 to 1:1).

Further, when three of the aprotic polar solvent (A), organic solvent (C) and water (W1) are used upon preparation of "a solution or suspension containing Compound (I) or a salt thereof and the aprotic polar solvent (A)", it is preferable that a mixing volume ratio (aprotic polar solvent (A) /organic solvent (C)/water (W1)) is 2 to 10/2 to 10/1.

Examples of a method of crystallization include a method of stirring the solution or suspension, a method of adding a seed crystal to the solution or suspension, a method of changing the temperature of the solution or suspension, a method of changing the solvent composition of the solution or suspension, a method of reducing the amount of the solution or suspension, and a method of combining two or more of these methods.

Examples of the "method of stirring the solution or suspension" include a method of stirring a solution or suspension containing Compound (I) or a salt thereof at about 0 to about 50° C., preferably at room temperature or lower (about 0° C. to about 30° C.) for about 0.01 to 100 hours, preferably about 0.1 to 30 hours.

The objective substance is unstable to heat, and is rapidly decomposed by heating. However, since the process of the present invention do not particularly require heating procedures, and can afford an objective crystal by crystallization at around room temperature, this process is extremely excellent as an industrial process.

Examples of the "method of adding a seed crystal to the solution or suspension" include a method of adding Compound (I) or a salt thereof as a seed crystal to the solution or suspension containing Compound (I) or a salt thereof.

Examples of the "method of changing the temperature of the solution or suspension" include a method of changing, preferably cooling the temperature of the solution or suspension containing Compound (I) or a salt thereof (e.g. lowering a temperature of the liquid by 5 to 100° C.), and a method of heating (e.g. raising a temperature of the liquid by 5 to 100° C.), followed by cooling (e.g. lowering a temperature of the liquid by 5 to 100° C.).

Examples of the "method of changing the solvent composition of the solution or suspension" include a method of mixing the solution or suspension containing Compound (I) or a salt thereof with water (W2) and/or the organic solvent (B) (e.g. solvents described in a class 2 or 3 of guideline of International Conference on Harmonisation of Pharmaceutical for Human USE (ICH), such as esters, ketones, phenols, alcohols, ethers, aromatic hydrocarbons, amides, sulfoxides, hydrocarbons, nitriles, halogenated hydrocarbons, pyridines and a mixture of two or more (preferably two to five, more preferably two to three) of them; preferably ketones, acetic acid esters, alcohols, ethers and hydrocarbons and a mixture of two or more (preferably two to five, more preferably two to three) of them; particularly preferably acetone, ethyl acetate, methanol, ethanol, propanol, tert-butyl methyl ether, hexane and heptane).

Inter alia, (1) a method of mixing with water (W2), or (2) a method of mixing with the organic solvent (B) is preferable.

As one aspect, the organic solvent (B) is a mixed solvent of one or more (preferably two to five, more preferably two or three) organic solvents (herein, two or more of the organic solvents are referred to as "organic solvent (B1)" or "organic solvent (B2)" in some cases). When two or more organic solvents are used, they may be mixed into "a solution or suspension containing Compound (I) or a salt thereof" simultaneously, or plural organic solvents may be mixed at different times.

A preferable aspect includes, for example, a method of (1) mixing with one or more organic solvent(s) (B1) selected from acetone, ethyl acetate, methanol, ethanol and propanol and, thereafter, (2) mixing with one or more organic solvent (s) (B2) selected from heptane, hexane and tert-butyl methyl ether.

Further, when both of water (W2) and the organic solvent (B) are mixed with "a solution or suspension containing Compound (I) or a salt thereof", water (W2) and the organic solvent (B) may be mixed with "a solution or suspension containing Compound (I) or a salt thereof" simultaneously, or they may be mixed at different times. In such the case, when two or more (preferably two to five, more preferably two or three) organic solvents (B) are used, the two or more organic solvents (B) may be mixed in advance and, thereafter, the mixture may be mixed with mixing with water (W2) at the same time or at a different time, alternately, the two or more organic solvents (B) may be separately mixed with mixing with water (W2), at the same time or at different times.

As a method of mixing "the solution or suspension containing Compound (I) or a salt thereof" with "water (W2) and/or the organic solvent (B)", "the solution or suspension containing Compound (I) or a salt thereof" and "water (W2) and/or the organic solvent (B)" may be mixed and stirred at once according to the process known per se, but a preferable method is a method of adding dropwise water (W2) or the organic solvent (B) or a mixture thereof to the solution or suspension containing Compound(I) or a salt thereof under stirring, alternately preferably adding dropwise the solution or suspension containing Compound (I) or a salt thereof to water (W2) or the organic solvent (B) or a mixture thereof under stirring.

Upon carrying out such "method of changing the solvent composition of the solution or suspension", the temperature at which water (W2) and/or the organic solvent (B) are mixed with the solution or suspension containing Compound (I) or a salt thereof, is about 0 to about 50° C., preferably room temperature (about 0° C. to about 30° C.)

When the organic solvent (B) is used, it is preferable to use the organic solvent (B) at 1 to 10-fold amount (volume), preferably 1 to 5-fold amount (volume) of the aprotic polar solvent (A).

In addition, when water (W2) is used, it is preferable to use water (W2) at 0.1 to 3-fold amount (volume), preferably 0.5 to 2-fold amount (volume) of the aprotic polar solvent (A).

Further, when water (W2) and the organic solvent (B) are used together, a mixing volume ratio is 1:50 to 5:1, preferably 1:25 to 3:1.

Examples of the "method of reducing the amount of the solution or suspension" include a method of distilling off or evaporating the solvent from the solution or suspension containing Compound (I) or a salt thereof and the aprotic polar solvent (A).

Among them, preferable are:
(i) a method of stirring the solution or suspension,
(ii) a method of changing the solvent composition of the solution or suspension,
(iii) a method of carrying out both of a method of stirring the solution or suspension and a method of adding a seed crystal to the solution or suspension,
(iv) a method of carrying out both of a method of stirring the solution or suspension and a method of changing the temperature of the solution or suspension,
(v) a method of carrying out both of a method of stirring the solution or suspension and a method of changing the solvent composition of the solution or suspension,
(vi) a method of carrying out both of a method of stirring the solution or suspension and a method of reducing the amount of the solution or suspension,
(vii) a method of carrying out a method of stirring the solution or suspension, a method of changing the temperature of the solution or suspension and a method of adding a seed crystal to the solution or suspension concurrently,
(viii) a method of carrying out a method of stirring the solution or suspension, a method of changing the solvent composition of the solution or suspension and a method of adding a seed crystal to the solution or suspension concurrently,
(ix) a method of carrying out a method of stirring the solution or suspension, a method of reducing the amount of the solution or suspension and a method of adding a seed crystal to the solution or suspension concurrently, (x) a method of carrying out a method of stirring the solution or suspension, a method of changing the temperature of the solution or suspension and a method of changing the solvent composition of the solution or suspension concurrently, (xi) a method of carrying out a method of stirring the solution or suspension, a method of changing the temperature of the solution or suspension and a method of changing the solvent composition of the solution or suspension and a method of adding a seed crystal to the solution or suspension concurrently, (xii) a method of carrying out a method of stirring the solution or suspension, a method of changing the temperature of the solution or suspension and a method of reducing the amount of the solution or suspension, and (xiii) a method of carrying out a method of stirring the solution or suspension, a method of changing the temperature of the solution or suspension, a method of reducing the amount of the solution or suspension and a method of adding a seed crystal to the solution or suspension.

Inter alia, methods of (ii), (v) and (x) are preferable, and a method of (v) is more preferable.

The crystallized crystal can be collected by a method such as filtration and centrifugation. A crystallized crystal may be subjected to recrystallization once or two or more times (preferably 2 to 3 times) as it is, or if needed, after washing or drying. Specifically, a crystallized crystal may be dissolved or suspended in a solvent containing the aprotic polar solvent (A), followed by being further crystallized once or two or more times according to the aforementioned method, or it may be recrystallized once or two or more times from esters (e.g. ethyl acetate etc.), alcohols (e.g. methanol, ethanol, propanol etc.), hydrocarbons (e.g. hydrocarbon having a carbon number of 5 to 8 such as hexane and heptane), ethers (e.g. tert-butyl methyl ether etc.), water or a mixed solvent of two or more (preferably two to three) of them.

Such recrystallization may be carried out by dissolving or suspending a crystallized crystal in esters (e.g. ethyl acetate etc.), alcohols (e.g. methanol, ethanol, propanol etc.), hydrocarbons (e.g. hydrocarbon having a carbon number of 6 to 8 such as hexane and heptane), ethers (e.g. tert-butyl methyl ether), water or a mixed solvent of two or more (preferably two to three) of them and, thereafter, carrying out the aforementioned method such as method of stirring the solution or suspension, method of adding a seed crystal to the solution or suspension, method of changing the temperature of the solution or suspension, method of changing the solvent composition of the solution or suspension, method of reducing the amount of the solution or suspension, or method of combining two or more of these methods (specifically, methods according to the above-mentioned above (i) to (xiii)).

When the finally obtained crystal is used in preparing an injectable, the process of the present invention preferably further comprises a step of removing pyrogens and/or a sterilizing step.

A step of removing pyrogens refers to a step of removing pyrogens such as endotoxin and the like by passing through an ultrafiltration equipment or a filter such as Posidyne. The step will be explained more specifically by referring to two examples.

(1) A crystal of Compound (I) is dissolved, for example, in about 1 to about 5 equivalent (preferably about 1.5 to about 3 equivalent) of aqueous alkali solution such as sodium hydroxide relative to Compound (I), and the solution is passed through an ultrafiltration equipment (ultrafiltration module SIP-0013 manufactured by Asahi Chemical Industry Co., Ltd.).

(2) (i) A crystal of Compound (I), (ii) an aprotic polar solvent such as THF and (iii) water are mixed to dissolve, and the solution is passed through Posidyne filter (Posidyne SLK7002NFZP manufactured by Pall Corporation).

It is preferable that a mixing volume ratio of an aprotic polar solvent and water (aprotic polar solvent: water) is 20:1 to 5:1 (preferably 12:1 to 7:1).

A sterilizing step refers to a step of removing bacteria by passing through a membrane or a filter such as Posidyne. This step will be explained more specifically by referring to two examples.

(1) (i) Compound (I) or a salt thereof, (ii) an aprotic polar solvent such as THF and (iii) water are mixed to dissolve, and the solution is passed through a membrane filter (Ultipor N66, SLK7002NFP manufactured by Pall Corporation).

It is preferable that a mixing volume ratio of an aprotic polar solvent and water (aprotic polar solvent: water) is 20:1 to 5:1 (preferably 12:1 to 7:1).

(2) (i) Compound (I) or a salt thereof, (ii) an aprotic polar solvent such as THF and (ii) water are mixed to dissolve, and the solution is passed through Posidyne filter (PosidyneSLK7002NFZP manufactured by Pall Corporation).

It is preferable that a mixing volume ratio of an aprotic polar solvent and water (aprotic polar solvent: water) is 20:1 to 5:1 (preferable 12:1 to 7:1).

Examples of a method of washing the objective crystal collected by a method such as filtration and centrifugation include a method of mixing the resulting wet crystal with water, alcohols (e.g. methanol, ethanol etc.) ketones (e.g. acetone etc.) esters (e.g. ethyl acetate etc.) or a mixed solvent of two or more of them, followed by stirring the mixture for 0.1 to 10 hours, preferably 0.5 to 5 hours.

Examples of a method of drying the objective crystal collected by a method such as filtration and centrifugation include drying under reduced pressure, drying under ventilation, drying with heating, and natural drying.

The characteristics of the crystal obtained by the process of the present invention are as follows:

(1) The crystal contains 5000 ppm or less (preferably 1000 ppm or less, more preferably 720 ppm or less) of an aprotic polar solvent such as THF.

(2) The crystal does not substantially contain a tin compound (particularly, organotin compound).

Herein, "does not substantially contain a tin compound" means that a content of a tin compound in the crystal is 1000 ppm or less, preferably 100 ppm or less, more preferably 10 ppm or less.

(3) The crystal does not substantially contain an analogue of Compound (I).

Herein, "does not substantially contain an analogue of Compound (I)" means that a content of an analogue (e.g. ketone compound, ethyl ester compound) of Compound (I) in the crystal is 1% or less, preferably 0.8 or less, more preferably 0.5% or less.

(4) The crystal does not substantially contain residual organic solvent.

The residual organic solvent is a solvent used in a step of producing Compound (I) or a salt thereof such as dichloromethane, methanol and acetone, and "does not substantially contain residual organic solvent" means that a total content of the residual organic solvents in the crystal is 5000 ppm or less, preferably 1000 ppm or less, more preferably 500 ppm or less, and the amount of residual dichloromethane is less than 50 ppm.

(5) The crystal is substantially pyrogen-free.

"Substantially pyrogen-free" means that, when the crystal is tested according to Japanese Pharmacopoeia, a general test method "endotoxin test method", the amount of endotoxin in Compound (I) is 1.25EU/mg or less.

(6) The crystal is substantially sterile.

"Substantially sterile" means that the number of existing living bacteria in Compound (I) is 0/g.

Compound (I) can also be purified by the following (A) or (B) method.

(A) An objective crystal of Compound (I) can be produced by dissolving or suspending Compound (I) or a salt thereof in heated alcohols (e.g. methanol, ethanol etc.; preferably ethanol) or mixed solvent with water, followed by cooling the solution or suspension.

The temperature of the "heated alcohols or mixed solvent with water" is about 40° C. to about 90° C., preferably about 60° C. to about 85° C.

A preferable solvent is ethanol or a mixed solvent of ethanol and water.

When recrystallized from a mixed solvent of alcohols and water, a mixing volume ratio (alcohols: water) is 30:1 to 3:1, preferably 15:1 to 5:1.

In "cooling", it is preferable that the temperature of the solution or suspension is lowered by about 10 to about 100° C., preferably about 50 to about 80° C.

Such the recrystallization procedure is carried out once or two or more times (preferably two to three times).

The resulting crystal is subjected to a hydrolysis reaction, preferably, using an aqueous alkali solution such as sodium hydroxide, potassium hydroxide, sodium methoxide, sodium ethoxide, potassium methoxide, and potassium ethoxide. The amount of alkali used in the hydrolysis reaction is about 2 to 5 equivalent relative to Compound (I). The hydrolysis reaction is carried out at a temperature of about 50 to about 100° C., preferably about 70 to about 90° C. under stirring. The reaction time is about 0.1 to about 10 hours, preferably about 1 to about 5 hours.

After subjecting to the hydrolysis reaction, the reaction solution is cooled to about –10 to 30° C., preferably about 0 to 10° C., and an acid (e.g. inorganic acid such as hydrochloric acid) is mixed (preferably added dropwise), if necessary, in the presence of alcohols such as methanol, thereby, the objective crystal can be obtained.

The crystallized crystal can be collected by a method such as filtration and centrifugation. The crystallized crystal may be dissolved or suspended in an aqueous alkali solution (e.g. aqueous sodium hydroxide solution) as it is or if necessary, after washing or drying, followed by mixing (preferably adding dropwise) with an acid (e.g. inorganic acid such as hydrochloric acid), if necessary, in the presence of alcohols such as methanol, and recrystallized once or two or more times (preferably two to three times).

When the finally obtained crystal is used for preparing an injectable, it is preferable that such process comprises the same step of removing pyrogens and/or sterilizing step as those described above.

Examples of a method of washing or drying a crystal include the same washing method and drying method as those described above.

(B) An objective crystal of Compound (I) can be produced by recrystallizing MET or a salt thereof, subjecting the resulting crystal of MET or a salt thereof to a hydrolysis reaction, and crystallizing a crystal.

The aforementioned recrystallization of MET or a salt thereof is carried out, for example, by dissolving or suspending MET or a salt thereof in heated ketones such as acetone or mixed solvent thereof with water, followed by cooling the solution or suspension.

The temperature of the "heated ketones or a mixed solvent thereof with water" is about 40° C. to about 80° C., preferably about 45° C. to about 70° C.

A preferable solvent is acetone or a mixed solvent of acetone and water.

When recrystallized from a mixed solvent of ketones and water, a mixing volume ratio (ketones: water) is 30:1 to 3:1, preferably 15:1 to 5:1.

It is preferable that, in "cooling", the temperature of the solution or suspension is lowered by about 30 to about 80° C., preferably about 40 to about 70° C.

Such recrystallization procedure is carried out once or two or more times (preferably two to three times.) The hydrolysis reaction is carried out, for example, by mixing the resulting crystal of MET or a salt thereof with an aqueous alkali solution, preferably, such as sodium hydroxide, potassium hydroxide, sodium methoxide, sodium ethoxide, potassium methoxide, and potassium ethoxide. The amount of alkali used in hydrolysis reaction is about 2 to 5 equivalents relative to MET or a salt thereof. The hydrolysis reaction is carried out at a temperature of about 40 to about 100° C., preferably about 55 to about 85° C. under stirring. The reaction time is about 0.1 to about 10 hours, preferably about 0.5 to about 5 hours.

After subjecting to the hydrolysis reaction, the objective crystal can be obtained by cooling the reaction solution to about –10 to about 30° C., preferably about –5 to about 15° C. and mixing (preferably adding dropwise) with acid (e.g. inorganic acid such as hydrochloric acid), if necessary, in the presence of alcohols such as methanol.

The crystallized crystal can be collected, for example, by a method such as filtration and centrifugation. The crystallized crystal may be dissolved or suspended in an aqueous alkali solution (e.g. aqueous sodium hydroxide solution) as it is or if necessary, after washing or drying, followed by mixing (preferably adding dropwise) with an acid (e.g. inorganic acid such as hydrochloric acid), if necessary, in the presence of alcohols such as methanol, and recrystallized once or two or more times (preferably two to three times).

It is preferable that such process comprises the same step of removing pyrogens and/or sterilizing step as those described above.

Examples of a method of washing or drying a crystal include the same washing method and drying method as those described above.

Examples of the "esters" include acetic acid $C_{1-4}$alkyl ester such as methyl acetate, ethyl acetate, propyl acetate, isopropyl acetate, butyl acetate and isobutyl acetate, and ethyl formate.

Examples of the "ketones" include acetone, methyl ethyl ketone, methyl isopropyl ketone, methyl butyl ketone and methyl isobutyl ketone.

Example of the "phenols" include anisole.

Examples of the "alcohols" include lower alcohols such as methanol, ethanol, 1-propanol, 2-propanol, 1-butanol, 2-butanol, 2-methyl-1-propanol, pentanol and 3-methyl-1-butanol; lower alcohols substituted with $C_{1-3}$alkoxy such as 2-methoxyethanol and 2-ethoxyethanol; ethylene glycol.

Examples of the "ethers" include tert-butyl methyl ether, diethyl ether, 1,1-diethoxypropane, 1,1-dimethoxypropane, 2,2-dimethoxypropane, isopropyl ether, tetrahydrofuran, and methyltetrahydrofuran.

Examples of the "aromatic hydrocarbons" include chlorobenzene, toluene, xylene and cumene.

Examples of the "aromatic hydrocarbons" include chlorobenzene, toluene, xylene, cumene.

Examples of the "amides" include formamide, N,N-dimethylacetamide, N,N-dimethylformamide and N-methylpyrrolidone.

Examples of the "sulfoxides" include dimethyl sulfoxide.

Examples of the "hydrocarbons" include $C_{3-10}$alkane such as propane, butane, pentane, hexane, heptane, octane and isooctane, preferably $C_{6-10}$alkane.

Examples of the "nitriles" include acetonitrile.

Examples of the "halogenated hydrocarbons" include $C_{1-6}$alkane optionally substituted with 1 to 5 halogens (e.g. fluorine, chlorine, bromine, iodine) such as chloroform, dichloromethane, dichloroethene and trichloroethene.

Examples of the "pyridines" include pyridine.

The crystal crystallized by the process of the present invention or a dried crystal thereof does not substantially contain an analogue substance, a tin compound, and a highly toxic solvent such as dichloromethane, is low in toxicity, and can be used as an agent for preventing or treating following diseases of a mammal (e.g. human, mouse, rat, rabbit, dog, cat, cow, pig, monkey, etc.), as it is or by formulating into a pharmaceutical composition by mixing with a pharmaceutically acceptable carrier.

Herein, as the pharmaceutically acceptable carrier, various organic or inorganic carrier materials which are conventional as a pharmacy material are used, and these materials are incorporated as an excipient, a lubricant, a binding agent and a disintegrating agent in a solid preparation; as a solvent, a solubilizer, a suspending agent, an isotonic, a buffer or a soothing agent in a liquid preparation, and the like. Further, if necessary, pharmacy additives such as antiseptic, an antioxidant, a colorant and a sweetener may be used.

Preferable examples of the excipient include lactose, white sugar, D-mannitol, D-sorbitol, starch, gelatinized starch, dextrin, crystalline cellulose, low substituted-hydroxypropyl cellulose, sodium carboxymethylcellulose, gum arabic, dextrin, plullan, light anhydrous silicic acid, synthetic aluminium silicate, and magnesium aluminate metasilicate.

Preferable examples of the lubricant include magnesium stearate, calcium stearate, talc and colloidal silica.

Preferable examples of the binding agent include gelatinized starch, sucrose, gelatin, gum arabic, methylcellulose, carboxymethylcellulose, sodium carboxymethylcellulose, crystalline cellulose, white sugar, D-mannitol, trehalose, dextrin, plullan, hydroxypropyl cellulose, hydroxypropyl methylcellulose, and polyvinylpyrrolidone.

Preferable examples of the disintegrating agent include lactose, white sugar, starch, carboxymethylcellulose, calcium carboxymethylcellulose, croscarmellose sodium, sodium carboxymehtylstarch, light anhydrous silicic acid, low substituted-hydroxypropyl cellulose.

Preferable examples of the solvent include water for injection, physiological saline, Ringer's solution, alcohol, propylene glycol, polyethylene glycol, sesame oil, corn oil, olive oil, and cotton seed oil.

Preferable examples of the solubilizer include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferable examples of the suspending agent include surfactants such as stearyltriethanolaimne, sodium laurylsulfate, laurylaminopropionic acid, lecithin, benzalkonium chloride, benzethonium chloride, and glyceryl monostearate; hydrophilic polymers such as polyvinyl alcohol, polyvinylpyrrolidone, sodium carboxymethylcellulose, methylcellulose, hydroxymethylcellulose, hydroxyethylcellulose, and hydroxypropyl cellulose; polysorbates, and polyoxyethylene hydrogenated castor oil.

Preferable examples of the isotonic include sodium chloride, glycerin, D-mannitol, D-sorbitol, and glucose.

Preferable examples of the buffer include buffers such as phosphate, acetate, carbonate, citrate.

Preferable examples of the soothing agent include benzyl alcohol.

Preferable examples of the antiseptic include paraoxybenzoic acid esters, chlorobutanol, benzyl alcohol, phenethyl alcohol, dehydroacetic acid, sorbic acid.

Preferable examples of the antioxidant include sulfite, and ascorbate.

Preferable examples of the colorant include water-soluble edible tar pigments (e.g. edible pigments such as edible red Nos.2 and 3, edible yellow Nos.4 and 5, edible blue Nos.1 and 2), water-insoluble lake pigments (e.g. aluminium salt of the aforementioned water-soluble edible tar pigments), and natural pigments (e.g. β-carotene, chlorophyll, bengala).

Preferable examples of the sweetener include saccharine sodium, dipotassium glycyrrhizin, aspartame, and stevia.

Examples of a dosage form of a pharmaceutical composition include oral agents such as tablets, capsules (including soft capsule, and microcapsule), granule, powders, syrups, emulsions and suspensions; and parenteral agents such as injectables (e.g. subcutaneous injectables, intravenous injectables, muscular injectables, intraperitoneal injectables, intravitreous injectables), drip infusions, external preparations (e.g. transnasal preparations, transdermal preparations, and ointments), suppositories (e.g. rectal suppositories, vagina suppositories), pellets, drip infusions, and sustained-release preparations, and these can be safely administered orally or parenterally, respectively.

A pharmaceutical composition can be prepared by the method which is conventional in the pharmacy technical field, for example, by the method described in Japanese Pharmacopoeia. In follows, a specific method of preparing preparations will be described in detail.

For example, oral agents are prepared by adding, for example, an excipient (e.g. lactose, white sugar, starch, D-mannitol etc.), a disintegrating agent (e.g. calcium carboxymethylcellulose etc.), a binding agent (e.g. gelatinized starch, gum arabic, carboxymethylcellulose, hydroxypropyl cellulose, polyvinylpyrrolidone etc.) or a lubricant (e.g. talc, magnesium stearate, polyethylene glycol 6000 etc.) to an active ingredient, followed by compression-molding, and, then, if necessary, coating using a coating base material by the known method per se for the purpose of masking of taste, dissolution in intestine or sustainment.

Examples of the coating base material include a sugar coating base material, a water-soluble film coating base material, an enteric film coating base material, and a sustained-release film coating base material.

As the sugar coating base material, white sugar is used and, further, one or more selected from talc, precipitated calcium carbonate, gelatin, gum arabic, plullan and carnauba wax may be used jointly.

Examples of the water-soluble film coating base material include cellulose polymers such as hydroxypropyl cellulose, hydroxypropyl methylcellulose, hydroxyethylcellulose, and methyl hydroxyethylcellulose; synthetic polymers such as polyvinylacetal diethylaminoacetate, aminoalkyl methacrylate copolymer E [Eudragit E (trade name), manufactured by Rohmpharm], and polyvinylpyrrolidone; polysaccharides such as plullan.

Examples of the enteric film coating base material include cellulose polymers such as hydroxypropyl methylcellulose phthalate, hydroxypropyl methylcellulose acetate succinate, carboxymethyl ethylcellulose, and cellulose acetate phthalate; acrylic acid polymers such as methacrylic acid copolymer L [Eudragit L (trade name), Rohmpharm], methacrylic acid copolymer LD [Eudragit L-30D55 (trade name), Rohmpharm], and methacrylic acid copolymer S [Eudragit S (trade name), Rohmpharm]; natural substances such as shellac.

Examples of the sustained-release film coating base material include cellulose polymers such as ethylcellulose; acrylic acid polymers such as aminoalkyl methacrylate copolymer RS [Eudragit RS (trade name), Rohmpharm], ethyl acrylate-methyl methacrylate copolymer suspension [Eudragit NE (trade name), Rohmpharm].

The aforementioned coating base materials may be used with mixing two or more of them at an appropriate ratio. Alternatively, upon coating, a light-resistant agent such as titanium oxide, iron sesquioxide and the like may be used.

The injectable is prepared by dissolving, suspending or emulsifying an active ingredient together with a dispersing agent (e.g. Polysorbate 80, polyoxyethylene hydrogenated castor oil 60 etc.), polyethylene glycol, carboxymethylcellulose, sodium alginate etc.), a preservative (e.g. methylparaben, propylparaben, benzyl alcohol, chlorobutanol, phenol etc.), and an isotonic (e.g. sodium chloride, glycerin, D-mannitol, D-sorbitol, glucose etc.) in an aqueous solvent (e.g. distilled water, physiological saline, Ringer's solution etc.) or in an oily solvent (e.g. vegetable oils such as olive oil, sesame oil, cotton seed oil, and corn oil, propylene glycol etc.). Thereupon, if desired, additives such as a solubilizer (e.g. sodium salicylate, sodium acetate etc.), a stabilizing agent (e.g. human serum albumin etc.), a soothing agent (e.g. benzyl alcohol etc.) and the like may be used.

The pharmaceutical composition of the present invention is preferably formulated into a sustained-release preparation.

Examples of such sustained release preparation include:

[1] a sustained-release preparation containing Compound (I) or a salt thereof, and a biodegradable polymer,

[2] the sustained-release preparation described in [1], wherein the biodegradable polymer is an α-hydroxycarboxylic acid polymer,

[3] the sustained-release preparation described in [1], wherein the α-hydroxycarboxylic acid polymer is a lactic acid-glycholic acid polymer,

[4] the sustained-release preparation described in [3], wherein the molar ratio of lactic acid and glycolic acid is 100/0 to 40/60,

[5] the sustained-release preparation described in [2], wherein the weight average molecular weight of the polymer is 3,000 to 50,000,

[6] the sustained-release preparation described in [1], which is for injection,

[7] the sustained-release preparation described in [1], which contains a multivalent metal,

[8] the sustained-release preparation described in [7], wherein the multivalent metal is zinc, and

[9] a sustained-release preparation containing Compound [I] or a salt thereof, a biodegradable polymer and a multivalent metal.

Such sustained-release preparation is prepared and used according to the method described in EP-A-1058541.

Examples of another aspect of sustained-release preparations include:

[1] a sustained-release preparation containing Compound (I) or a salt thereof, a component obtained by treating a water-hardly soluble multivalent metal compound with water, and a biodegradable polymer,

[2] the sustained-release preparation described in [1], wherein the biodegradable polymer is an a-hydroxycarboxylic acid polymer,

[3] the sustained-release preparation described in [2], wherein the α-hydroxycarboxylic acid polymer is a lactic acid-glycholic acid polymer,

[4] the sustained-release preparation described in [3], wherein the molar ratio of lactic acid and glycolic acid is 100/0 to 40/60,

[5] the sustained-release preparation described in [2], wherein the weight average molecular weight of the polymer is 3,000 to 50,000,

[6] the sustained-release preparation described in [1], which is for injection,

[7] the sustained-release preparation described in [1], wherein the multivalent metal is zinc,

[8] the sustained release preparation described in [1], wherein the multivalent metal compound is zinc oxide,

[9] the sustained-release preparation described in [1], which further contains a multivalent metal, and

[10] the sustained-release preparation described in [9], wherein the multivalent metal is zinc.

Such sustained-release preparation is prepared and used according to the method described in WO 01/60410 (PCT/JP01/01191).

A dose of Compound (I) or a pharmaceutically acceptable salt thereof differs depending on administration subject, administration route, subject disease, symptom, and the like, and for example, when orally administered to a mammal (e.g. human, cow, pig, dog, cat, mouse, rat, rabbit etc.), in particular an adult (body weight 50 kg), one time amount of Compound (I) or a pharmaceutically acceptable salt thereof as an active ingredient is usually about 0.001 to 500 mg, preferably 0.1 to 50 mg, and it is desirable to administer this amount once to three times per day.

On the other hand, when the pharmaceutical composition of the present invention is formulated into a sustained-release preparation, a dose thereof differs variously depending on the content of Compound (I) as base medicament, a dosage form, a duration time of physiologically active compound release, a subject disease, and a subject animal, and may be an effective amount of physiologically active compound. For example, when the sustained-release preparation is a one month preparation, a dose per one time of physiologically active compound as base medicament can be appropriately selected from a range, preferably, of about 0.01 mg to 10 mg/kg body weight, more preferably about 0.05 mg to 5 mg/kg body weight per adult.

A dose per one time of a sustained-release preparation can be appropriately selected from a range, preferably, of about 0.05 mg to 50 mg/kg body weight, more preferably about 0.1 mg to 30 mg/kg body weight per adult.

An administration time can be appropriately selected depending on the content of Compound (I) or a salt thereof, dosage form, duration time of physiologically active compound release, subject disease, and subject animal, from, for example, once per a few weeks, once per month, once per a few months (e.g. 3 months, 4 months, 6 months), and the like.

In addition, when the pharmaceutical composition of the present invention is formulated into a sustained-release preparation, the preparation may be also advantageously used by a bedridden patient, a patient with dementia, pharynx•esophagus disease, digestive disorder, or ingestion•swallowing disorder, or a patient who is difficult or impossible to treat with internal medicine, such as a patient at operation.

Examples of targeting disease of Compound (I) or a salt thereof as a physiologically active compound include diseases which are developed, or whose development is promoted, by constriction and proliferation of blood vessel or organ disorder developed via an angiotensin II receptor, by the presence of angiotensin II, or by factors induced by the presence of angiotensin II.

Examples of such diseases include systemic diseases such as hypertension, blood pressure in day variation abnormality, cardiac disease (hypercardia, acute heart failure, chronic heart failure including congestive, cardiomyopathy, angina, myocarditis, arrhythmia, tachycardia, cardiac infarction etc.), cerebrovascular disorder (silent cerebrovascular disorder, transient cerebral ischemic ceager, cerebral stroke, cerebrovascular dementia, hypertensive encephalopathy etc.), cerebral edema, cerebral circulation disorder, recurrence and sequela of cerebrovascular disorder (neurotic, mental symptomatic, subjective symptom, daily life activity disorder etc.), ischemic peripheral circulation disorder, cardiovascular ischemia, vain dysfunction, heart failure progression after cardiac infarction, diabetes, diabetic complex (diabetic retinopathy, diabetic nephropathy, diabetic neuropathy etc.), renal disease (nephritis, glomerular nephritis, glomerulosclerosis, renal insufficiency, thrombotic microangiopathy, dialysis complex, organ disorder including nephropathy due to radiation irradiation etc.), arteriosclerosis including atherosclerosis (aneurysm, coronary sclerosis, cerebral atherosclerosis, peripheral atherosclerosis etc.), vascular hypertrophy, vascular hypertrophy or occlusion and organ disorder after intervention (transdermal coronary plasty, stent dwelling, coronary endscope, intravascular ultrasound, coronary injection thrombolytic therapy etc.), vascular reocclusion•restenosis after bypass operation, erythrocytosis•hypertension•organ disorder•vascular hypertrophy after transplantation, rejection reaction after transplantation, ocular disease (glaucoma, hyper-ocular tension etc.), thrombosis, multiple organ failure, endothelium dysfunction, hypertensive susurrus aurium, other circulatory diseases (deep venous thrombosis, obstructive peripheral circulation disorder, arteriosclerosis obliterans, thromboangiitis obliterans, ischemic cerebral circulation disorder, Raynaud's disease, Paget's disease etc.), metabolism•nutrient disorder (obesity, hyperlipemia, hypercholeuterolemia, diabetes, glucose tolerance abnormality, hyperuricemia, hyperkalemia, hypernatremia etc.), neural denaturation disease (Alzheimer's disease, Parkinson's disease, amyotrophic lateral sclerosis, AIDS encephalopathy etc.), central nervous disorder (disorder such as cerebral hemorrhage and cerebral infarction and sequela•complex thereof, head trauma, spinal injury, cerebral edema, sensory dysfunction, sensory function abnormality, autonomic nerve dysfunction, autonomic nerve function abnormality, multiple sclerosis etc.), dementia, memory disorder, consciousness disorder, amnesia, anxiety, tension symptom, disphoria mental status, mental disease (depression, epilepsy, alcohol dependency etc.), inflammatory disease (diabetic complex such as retinophathy, nephropathy, nervous disorder, great vessel disorder etc.; arthritis such as chronic rheumatoid arthritis, osteoarthritis, rheumatoid myelitis, periostosteitis; inflammation after operation•trauma; remission of enlargement; pharyngitis; urocystitis; neuamonia, atopic dermatitis; inflammatory bowel disease such as Crohn's disease, ulcerous colitis etc.; meningitis; inflammatory ocular disease; inflammatory pulmonary disease such as pneumonia, pneumosilicosis, pulmonary sarcoidosis, pulmonary tuberculosis etc.), allergy disease (allergic rhinitis, conjunctivitis, gastrointestinal tract allergy, pollinosis, anaphylaxis etc.), chronic obstructive pulmonary disease, pneumonitis, carinii pneumonia, collagenosis (e.g. systemic lupus erythematosus, scleroderma, multiple arteritis etc.), liver disease, (hepatitis including chronic, cirrhosis), portal hypertension, digestive disorder (gastritis, gastric ulcer, gastric cancer, disorder after gastric operation, dyspepsia, esophageal ulcer, pancreatitis, large intestine polyp, cholelithiasis, hemorrhoids disease etc.), blood•hematopoietic organ disorder (polycythemia, vascular purpura, autoimmune hemolytic anemia, disseminated intravascular coagulation syndrome, multiple myelosis etc.), bone disease (e.g. fracture, refracture, osteoporosis, osteomalacia, bone Behcet's disease, tetania myelitis, chronic rheumatoid arthritis, knee osteoarthritis and destruction of joint tissue in their similar diseases), solid tumor, tumor (malignant melanoma, malignant lymphoma, digestive organ (e.g. stomach, intestine etc.) cancer etc.), cancer and cachexia accompanied therewith, metastasis of cancer, endocrine disease (Addison's disease, Cushing's syndrome, melanocytoma, primary aldosteronism etc.), Creutzfeldt-Jakob disease, urinary organ•male sexual organ disease (urocyspitis, prostatomegaly, prostate cancer, sexual infectious disease etc.), gynecological disease (menopausal disorder, pregnant toxicosis, endometriosis, hysteromyoma, ovary disease, mammary gland disease, sexual infectious disease etc.), diseases due to environmental•occupational factors (radiation disorder, disorder due to ultraviolet ray•infrared ray•laser light, altitude sickness etc.), respiratory disease (cold syndrome, pneumonia, asthma, pulmonary hypertension, pulmonary thrombus•pulmonary embolus etc.), infectious disease (virus infectious disease such as cytomegalovirus, influenzavirus, herpesvirus etc., Rickettsia infectious disease, bacteria infectious disease etc.), toxemia (sepsis, septic shock, endotoxin shock, Gram-negative sepsis, toxin shock syndrome etc.), otorhinolaryngological disease (Ménière's syndrome, susurrus aurium, gestation disorder, vertigo, balance disorder, swallowing disorder etc.), skin disease (keloid, angioma, psoriasis etc.), dialysis hypotension, myasthenia gravis, and chronic fatigue syndrome.

In addition, by suppressing the action of angiotensin II for a long time, disorders or abnormalities of the living body functions and the physiological actions which causes various diseases accompanied with adult diseases or aging can be improved or facilitation thereof can be inhibited, and diseases or pathologies derived from them can be primarily and secondarily prevented, or progression thereof can be suppressed. Examples of such disorders or abnormalities of living body functions and the physiological actions include disorders or abnormalities of cerebral circulation•renal circulation automatic regulating ability, circulation disorder (peripheral, cerebral, microcirculatory etc.), disorders of brain-blood barrier, reduction in insulin sensitivity, abnormalities of salt sensitivity, and coagulation•fibrinolytic system, character abnormality of blood•hemocyte components (platelet aggregating ability facilitation, abnormalities of erythrocyte deforming ability, facilitation of lymphocyte adhering ability, increase in blood viscosity etc.), enhancement of production and action of growth factor and cytokines (PDGF, VEGF, FGF, interleukin, TNF-α, MCP-1 etc.), enhancement of production and infiltration of inflammatory cells, enhancement of free radical production, promotion of fat sedimentation, endothelium function disorder, disorders of endothelium, cell and organ, edema, change in form of cells such as smooth muscle (form change into proliferating-type), enhancement of production and function of vessel agonistic substance and thrombus inducing substance (endothelin, thromboxane $A_2$ etc.), abnormal constriction of vessel etc., sugar tolerance abnormality, metabolism abnormality (serum lipid abnormality, blood sugar abnormality etc.), abnormal proliferation of cells etc., and vascularization (including abnormal angiogenesis in abnormal capillary network formation of atherosclerotic lesion tunica externa). Inter alia, Compound (I) or a salt thereof can be advantageously used as a primary or secondary preventing or treating agent for organ disorders accompanied with various disease (e.g., cerebrovascular disorders and organ disorders accompanied therewith, organ disorders accompanied with circulatory diseases, organ disorders accompanied with diabetes, organ disorders after intervention etc.).

Further, Compound (I) or a salt thereof can be advantageously used as an agent for preventing or treating portal vein pressure facilitation.

Esophageal varix rapture is known to occur frequently at night (Hepatology 1994; 19:595–601). In the pharmaceutical composition (preferably, sustained-release preparation) of the present invention, since the constant concentration in blood can be maintained day and night, not only dose and administration time can be reduced, but also stable reduction in portal vein pressure can be expected because of small variation of drug concentration in blood, as compared with administration by oral preparation. The above characteristics of the present pharmaceutical composition show usefulness as a drug for preventing varix rapture in esophagus and stomach. In addition, since symptom change due to ingestion interruption does not occur, the therapeutic effect is expected to be clearer. Further, the pharmaceutical composition of the present invention is expected to be effective for promoting production of HGF (Hepatocyte Growth Factor), and contribution to liver regeneration and liver function recovery can be expected.

In addition, by maintaining constant blood concentration of Compound (I) or a salt thereof day and night, the effect of prevention or treatment for cerebrovascular disorder such as cerebral infarction is expected to be clearer.

The pharmaceutical composition of the present invention may be used together with diuretic depressor (oral preparation) which is usually used together with an angiotensin II antagonist.

In addition, the pharmaceutical composition of the present invention may be used together with other drug ingredients including other lipid lowering drug or cholesterol lowering drug, HMG-Co A reductase (3-hydroxy-3-methylglutaryl coenzyme A reductase) inhibitor, insulin sensitivity improver, bone disease treating drug, cardiac muscle protecting drug, coronary disease treating drug, other hypertension treating drug, chronic heart failure treating drug, diabetes treating drug, liver disease treating drug, gastric•duodenal ulcer treating drug, biliary disease treating drug, thyroid gland hypofunction treating drug, nephrotic syndrome treating drug, chronic renal failure treating drug, gynecologic disease treating drug, urinary organ•male sexual organ disease treating drug and infectious disease treating drug. In this case, these compounds may be administered as an oral preparation or, if necessary, may be administered in the form of a suppository as rectal preparation. Examples of an ingredient which can be combined in this case include fibrates [e.g. clofibrate, benzafibrate, gemfiprozil etc.], nicotinic acid, a derivative or an analog thereof [e.g. acipimox and probucol], bile acid binding resin [e.g. cholestyramin, colestipol etc.], a compound which suppresses cholesterol absorption [e.g. sitosterol and neomycin], squaleneepoxydase inhibitor [e.g. NB-598 and analogous compound].

Still other possible components used in combination are oxide squalene-lanosterolcyclase, for example, a decalin derivative, an azadecalin derivative and an indane derivative.

Further, combinations with the following various treating drugs are possible:

hypertension treating drug: diuretic [e.g. furosemide (lasix), bumetanide (lunetoron), azosemide (diart)], depressor [e.g. ACE inhibitor, (enalapril maleate (renivace) etc.) and Ca antagonist (manidipine, amlodipine etc.), α or β receptor blocker etc.], and the like, chronic cardiac failure treating drug: cardiac [e.g. cardiotonic glycoside (digoxin etc.), β receptor stimulator (catecholamine preparation such as denopamine and dobutamine) and PDE inhibitor etc.], diuretic [e.g. furosemide (lasix), spilonolactone (aldactone) etc.], ACE inhibitor, [e.g. enalapril maleate (renivace) etc.], Ca antagonist [e.g. amlodipine etc.] and β receptor blocker, and the like, anti-arrhythmia drug: disopyramide, lidocaine, quinidine sulfate, flecainide acetate, mexiletine hydrochloride, amiodarone hydrochloride, and β blocker, Ca antagonist, and the like, bone disease treating drug: calcium preparation (e.g. calcium carbonate etc.), calcitonin preparation, active vitamin $D_3$ preparation (e.g. alfacalcidol (alfarol etc.), calcitriol (rocaltrol) etc.), sex hormones (e.g. estrogen, estradiol etc.), hormone preparation [e.g. binding type estrogen (premarin) etc.], ipriflavone preparation (osten etc.), vitamin $K_2$, vitamin $K_2$ preparation [e.g. menatetrenone (glakay) etc.], bisphosphonic acid preparation (etidronate etc.), prostaglandin E2, fluorine compound (e.g. sodium fluoride etc.), osteogenic protein (BMP), fibroblast growth factor (FGF), platelet-derived growth factor (PDGF), transforming growth factor (TGF-β), insulin-like growth factor-1 and 2 (IGF-1, -2), parathyroid hormone (PTH), compounds described in EP-A1-376197, EP-A1-460488 and EP-A1-719782 (e.g. (2R, 4S)-(−)-N-[4-(diethoxyphosphorylmethyl)phenyl]-1,2, 4,5-tetrahydro-4-methyl-7,8-methylenedioxy-5-oxo-3-benzothiepin-2-carboxamide etc.), and the like;

diabetic treating drug: actos, rosiglitazone, kinedak, penfill, humulin, euglucon, glimicron, daonil, novolin, monotard, insulins, glucobay, dimelin, rastinon, pamilcon, deamelin S, iszilin, and the like;

liver disease treating drug: glycyrrhizin preparation [e.g. stronger minophagen etc.], hepatic hydrolysate, SH compound [e.g. glutathione etc.], special amino acid preparation [e.g. aminoleban etc.], phospholipid [e.g. polyene phosphatidylcholine etc.], vitamins [e.g. vitamins B1, B2. B6, B12, C etc.], adrenal cortical hormone [e.g. dexamethasone, betamethasone etc.], interferon [e.g. interferons α, β etc.], hepatogenic encephalopathy treating drug [e.g. lactulose etc.], and hemostat used at rapture of esophageal or gastric varix [e.g. vasopressin, somatostatin etc.] and the like;

gastric•duodenal ulcer treating drug: antacid [e.g. histamine H2 antagonist (cimetidine etc.), proton pump inhibitor (lansoprazole etc.)] and the like;

biliary disease treating drug: choleretic [e.g. dehydrocholic acid etc], and cholekinetic [e.g. magnesium sulfate etc.] and the like;

thyroid gland hypofunction treating drug: dry thyroid (thyreoid), levothyroxine sodium (thyradin S), liothyronine sodium (thyronine, cylmin) and the like;

nephrosis syndrome treating drug: usually, for steroid therapy which is adopted as first selection, prednisolone (predonine), prednisolone sodium succinate (predonine), methylprednisolone sodium succinate (solu-medrol), betamethasone (rinderon) and the like are used. And, for anti-coagulation therapy, anti-platelet drugs and anti-coagulant drugs such as dipyridamole (perusantin), dilazep hydrochloride (comelian), ticlopidine, clopidogrel, FXa inhibitor and the like are used;

HMG-Co A reductase inhibitor: cerivastatin, atrovastatin, pravastatin, simvastatin, itavastatin, lovastatin, fluvastatin, (+)-3R,5S-7-[4-(4-fluorophenyl)-6-isopropyl-2-(N-methyl-N-methanesulfonylamino)pyrimidin-5-yl]-3,5-dihydroxy-6 (E)-heptenoic acid and the like;

chronic renal failure treating drug: diuretic [e.g. furosemide (lasix), bumetanide (lunetoron), azosemide(diart)], depressor (e.g. ACE inhibitor (enalapril maleate (renivace)) and Ca antagonist (manidipine), α receptor blocker, (when administered by combining these compounds, the drugs can be used preferably orally);

thrombus formation preventing and treating drug: blood coagulation inhibitor (e.g. heparin sodium, heparin calcium, warfarin calcium (warfarin), blood coagulation factor Xa inhibitor and drug having the function of correcting balance of coagulation fibrinolytic system), thrombolytic drug [e.g. tPA, urokinase], anti-platelet drug [e.g. aspirin, sulfinpyrazone (Anturan), dipyridamole (perusantin), ticlopidine (panaldine), cilostazol(pletaal), GPIIb/IIIa antagonist (Reo Pro)] and the like;

coronary vasodilator: nifedipine, diltiazem, nicorandil, nitrous acid agent and the like;

cardiac muscular protecting drug: cardiac ATP-K opener, Na—H exchange inhibitor, endoserin antagonist, urotensin antagonist and the like;

anti-inflammatory drug: aspirin, acetaminophen, non-steroidal anti-inflammatory agent (e.g. indometacin etc.), steroid agent (e.g. dexamethasone etc.) and the like;

anti-allergy drug: anti-histamine drug [e.g. clorpheniramine maleate etc.], stimulation therapeutic [e.g. bucillamine, etc.], other azelastine hydrochloride, seratrodast, tranilast, oxatomide, stronger neo-minophagen c, tranexamic acid, ketothiphen fumarate and the like;

anti-tumor drug: alkylating agent, metabolism antagonist, anti-tumor antibiotic preparation, anti-tumor vegetable ingredient preparation, other anti-tumor drugs and the like;

central nerve acting drug: antianxiety agent, hypnotic and sedative drug, anesthetic, antispasmodic, autonomic drug, anti-Parkinson drug, other pychonervous drug, and the like;

gynecologic disease treating drug: e.g. climacteric disease treating drug (conjugated estrogen, estradiol, testosterone enanthate•estradiol valerate etc.), breast cancer treating drug (tamoxifen citrate etc.), endometriosis•hysteromyoma treating drug (leuprorelin acetate, Danazol etc.), and the like;

urinary organ•male sexual organ disease treating drug: e.g. prostatomegaly treating drug (tamsulosin hydrochloride, prazosin hydrochloride, chlormadinone acetate etc.), prostate cancer (leuprorelin acetate, goserelin acetate, chlormadinone acetate etc.), and the like;

infectious disease treating drug: e.g. antibiotic preparation (cefotiam hydrochloride, Cefozopran hydrochloride, ampicillin etc.), chemical treating agent (sulfa drug, synthetic antibacterial agent, anti-virus agent etc.), biological preparation (vaccines, blood preparations such as immunoglobulin etc.), and the like;

other anti-obesity drug (Mazindol etc.), anti-rheumatoid drug, and the like;

further, treatment by living body-derived various factors or gene-introduction thereof (e.g. ishemic disease treatment by vascularization promoting factors such as HGF, VEGF etc. or gene-introduction thereof) and the like.

When these drugs and the pharmaceutical composition of the present invention are used in combination, respective drugs may be incorporated into one composition (e.g. sustained-release preparation), or can be administered with the pharmaceutical composition of the present invitation (e.g. sustained release-preparation) at the same time or separately by formulating the aforementioned drugs by mixing with pharmacologically acceptable carriers, excipients, binders or diluents. When drugs are formulated into preparations separately, although the separately formulated preparations may be administered with mixing using diluents in use, separately formulated individual preparations may be administered to the same subject at the same time or separately at intervals.

The present invention will be further illustrated by the following Reference Examples and Examples, however, the present invention is not limited to these examples.

High performance liquid chromatography conditions (A)
Column: Nova-Pac C-18 (manufactured by Waters)
Mobile phase: (A) MeOH/$H_2$O/AcOH (50:50:1) (B) MeOH/$H_2$O/AcOH (90:10:1)
Gradient program: After the column is equilibrated with the mobile phase (A), a sample solution is injected. Immediately, composition is linearly changed so that the composition of the mobile phase becomes (B) in 40 minutes.
Flow rate: 0.8 mL/min
Detection: UV254 nm

EXAMPLES

Reference Example 1

Synthesis of methyl 2-[(2'-cyanobiphenyl-4-yl)methylamino]-3-nitrobenzoate[MBN]

23 g of 2-(4-methylphenyl)benzonitrile [MPB], 22 g of N-bromosuccinic acid imide [NBS] and 47 mg of 2,2'-azobis (2,4-dimethylvaleronitrile) were suspended in 44 ml of dichloromethane, and the reaction was allowed to proceed at 45 to 50° C. for 5 hours under stirring. 46 ml of water was added, and the layers were separated to obtain organic layer (The same procedure was carried out three times totally). The organic layer was concentrated, and 50 ml of acetonitrile was added. The solution was concentrated again, and 50 ml of acetonitrile was added thereto to obtain 116 g of a solution of 2-(4-bromomethylphenyl)benzonitrile [BMB] in acetonitrile (yield calculated from a quantitated value of 2-(4-bromomethylphenyl)benzonitrile: 84% ).

30.1 g of methyl 2-tert-butoxycarbonylamino-3-nitrobenzoate [BAN], 40.8 g of potassium carbonate and 160 ml of acetonitrile were added to the acetonitrile solution in which unreacted 2-(4-methylphenyl)benzonitrile [MPB] and 2-(4, 4-dibromomethylphenyl)benzonitrile as an analogue of BMB were contaminated, and the reaction was allowed to proceed at about 82° C. for about 5 hours under stirring. After cooling to room temperature, the precipitated crystals were filtered off, and the filtrate was concentrated to give methyl 2-[N-t-butoxycarbonyl-N-[(2'-cyanobiphenyl-4-yl) methyl]amino]-3-nitrobenzoate [BBN]. The concentrated material was dissolved in 190 g of methanol, and 106 g of concentrated hydrochloric acid was added dropwise thereto.

The resulting solution was heated to a reflux temperature over 2 hours, and stirred for 2 hours under reflux, whereby, the reaction was allowed to proceed. The reaction solution was cooled, and precipitated crystals were collected by filteration and dried to give 35.1 g of methyl 2-[N-(2'-cyanobiphenyl-4-yl)methylamino]-3-nitrobenzoate [MBN] (yield relative to 2-(4-methylphenyl)benzonitrile [MPB] was 76.1%)

Reference Example 2

Synthesis of methyl 2-carboxy-3-nitrobenzoate [MNA]

3-Nitrophthalic acid [NPA] (660 kg), trimethyl orthoformate (400 kg), concentrated sulfuric acid (115 kg) and methanol (1180 kg) were mixed, and the mixture was stirred with heating (59 to 65° C.) for about 15 to 20 hours under reflux. The reaction solution was cooled, and concentrated at 40° C. or lower under reduced pressure. The residue was cooled to 30° C. or lower, water (900 L) was added, and the mixture was cooled to 5° C. or lower. The precipitated crystals were separated by a centrifuge, washed with water, and dried at 50° C. for about 50 hours to give methyl 2-carboxy-3-nitrobenzoate [MNA] (666.8 kg, 94.7%).

mp. 166–168° C. $^1$H-NMR (200 MHz, CDCl$_3$) δ: 4.03 (3H, s), 7.74 (1H, t), 8.39 (1H, dd), 8.42(1H, dd)

Reference Example 3

Synthesis of methyl 2-t-butoxycarbonylamino-3-nitrobenzoate [BAN]

Methyl 2-carboxy-3-nitrobenzoate [MNA] obtained in Reference Example 2 (164 kg) was dissolved in dimethylformamide [DMF] (242 kg), diphenylphosphoryl azide [DPPA] (204 kg) was added thereto at room temperature, and triethylamine (87 kg) was added dropwise while maintaining at 20 to 35° C. After stirring at 20 to 30° C. for about 3 hours, t-butyl alcohol (930 kg) was added to the reaction solution. The temperature was risen to 85 to 90° C. over 3 to 5 hours, and the solution was stirred for 1 to 2 hours under reflux (85 to 90° C.). The reaction solution was cooled, concentrated, and the residue was dissolved in ethyl acetate (1400 L). The solution was washed successively with a mixture of 15% hydrochloric acid (160 L) and water (1890 L), water (660 L), 5% aqueous sodium bicarbonate solution (1100 kg) and water (660 L), and the organic layer was concentrated under reduced pressure. Methanol (300 kg) was added thereto, and concentrated under reduced pressure. A seed crystal (15 kg) and methanol (450 kg) were added to the residue, and the mixture was heated to 50 to 60° C. to dissolve it. After cooled to 5° C., crystals were separated, washed with cold methanol (100 L), and dried to give methyl 2-t-butoxycarbonylamino-3-nitrobenzoate [BAN] (187.0 kg, 86.7%). The mother liquor and the washing were concentrated under reduced pressure, and cooled. The precipitated crystals were centrifuged, washed with cold methanol, and dried to give second crystal of BAN.

$^1$H-NMR (200 MHz, CDCl$_3$) δ: 1.50(9H, s), 3,96(3H, s), 7.23(1H, t), 8.10(1H, dd), 8.17(1H, dd)

IR(KBr) cm$^{-1}$:3360, 1730, 1705, 1580, 1520, 1490, 1440, 1365, 1355, 1310, 1270, 1240, 1150, 870, 835, 770, 725, 705

Reference Example 4 (1)

Synthesis of 4-(2-bromomethylphenyl)benzonitrile [BMB]

2-(4-Methylphenyl)benzonitrile [MPB] (271 kg), N-bromosuccinic acid imide [NBS] (256 kg), 2,2'-azobis(2,4-dimethylvaleronitrile) [ABN-V] (543 kg) and methylene chloride (680 kg) were stirred at 45 to 50° C. under reflux, and the reaction was allowed to proceed until an area percentage of 4-(2-boromomethylphenyl)benzonitrile [BMB] with HPLC became 82% or more (about 2 to 5 hours). After the reaction solution was cooled to 38 to 42° C., methylene chloride (250 kg) was added. Water (540 L) was added, the layers were separated, the resulting aqueous layer was extracted with 50 kg of methylene chloride, and the organic layers were combined (this procedure was repeated three times totally). The methylene chloride layer was concentrated to about 700 L (about 2.5-fold volume of MPB) under atmospheric pressure (inner temperature: about 46° C.) Acetonitrile (about 640 kg) was added thereto, the resulting solution was concentrated to about 1100 L under reduced pressure (about 200 to 450 mmHg) while maintaining the inner temperature at 45 to 55° C. (desirably 45 to 50° C.). Then, acetonitrile (about 480 kg) was added, and the resulting solution was concentrated to about 500 L under reduced pressure (about 200 to 450 mmHg) while maintaining the inner temperature at 45 to 55° C. (desirably 45 to 50° C.). Acetonitrile (about 480 kg) was added to the residue, whereby the amount of solution came to about 1100 L, to give a solution containing 2-(4-bromomethylphenyl)benzonitrile [BMB], unreacted 2-(4-methylphenyl)benzonitrile [MPB] and 2-(4,4-dibromomethylphenyl)benzonitrile as an analogue of BMB in acetonitrile.

Reference Example 4 (2)

Synthesis of methyl 2-[N-t-butoxycarbonyl-N-[(2'-cyanobiphenyl-4-yl)methyl]amino]-3-nitrobenzoate [BBN]

Methyl 2-t-butoxycarbonylamino-3-nitrobenzoate [BAN] obtained in Reference Example 3 (354 kg), a solution of 4-(2-bromomethylphenyl)benzonitrile [BMB] in acetonitrile obtained in Reference Example 4 (1), and anhydrous potassium carbonate (475 kg) were added to acetonitrile (1600 kg), and the mixture was heated (80 to 85° C.) under reflux for about 5 hours. The reaction solution was cooled, and the insoluble were separated and washed with acetonitrile (320 kg). The filtrated washing was concentrated under reduced pressure to give concentrate of methyl 2-[N-t-butoxycarbonyl-N-[(2'-cyanobiphenyl-4-yl)methyl]amino]-3-nitrobenzoate [BBN].

Example 4 (3)

Synthesis of methyl 2-[[(2'-cyanobiphenyl-4-yl)methyl]amino]-3-nitrobenzoate [MBN]

The concentrate (methyl 2-[N-t-butoxycarbonyl-N-[(2'-cyanobiphenyl-4-yl)methyl]amino]-3-nitrobenzoate [BBN]) obtained in Reference Example 4(2) and methanol (3200 L) were mixed, and 35% concentrated hydrochloric acid (1050 L) was added at 30° C. or lower over about 4 hours. The mixture was heated to a reflux temperature (67 to 69° C.) at a temperature rising rate of 10° C./hour or lower, and stirred under reflux for about 1.5 hours. The reaction solution was cooled, methanol (800 L) was added thereto, and the solution was stirred at 3 to 10° C. for about 1 hour. The precipitated crystals ware separated, and washed with methanol, followed by drying to give methyl 2-[[(2'-cyanobiphenyl-4-yl)methyl]amino]-3-nitrobenzoate [MBN] (407 kg; yield relative to MPB was 75%).

mp. 140 to 141° C. $^1$H-NMR(200 MHz, DMSO-d$_6$)δ: 3.84(3H,s), 4.26(2H,m), 6.86(1H,t), 7.46(2H,d), 7.54–7.65 (4H,m), 7.79(1H,d), 7.95(1H,dd), 8.05–8.11(2H,m), 8.67 (1H,t)

Reference Example 5

Synthesis of methyl 3-amino-2-[[(2'-cyanobiphenyl-4-yl)methyl]amino]benzoate [MBA]

Methyl 2-[[(2'-cyanobiphenyl-4-yl)methyl]amino]-3-nitrobenzoate [MBN] (400 kg) obtained in Reference Example 4(3) and tetrahydrofuran [THF] (1080 kg) were mixed, and the MBN solution was stirred. Tin (400 kg) and 35% hydrochloric acid (1322 kg) were mixed, the mixture was stirred at 25 to 30° C. for about 5 hours, warmed to about 80° C. over about 3 hours, and stirred at about 80° C. for about 8 hours. The resulting stannous chloride solution was added dropwise to the MBN solution at 15 to 25° C. over 5 to 8 hours to carry out reduction reaction at 15 to 25° C. for 2 to 5 hours. After completion of the reaction, the pH of solution was adjusted to 12 with 24% sodium hydroxide (about 2000 L) and flaky sodium hydroxide (about 177 kg). The organic layer was separated, and washed twice with an aqueous sodium bicarbonate solution (950 L) and three times with an aqueous saturated sodium chloride solution (840 L). The organic layer was filtered through a 3μ filter, and the solvent was distilled off. The residue was dissolved in ethyl acetate (540 kg), and concentrated again to give concentrate of methyl 3-amino-2-[[(2'-cyanobiphenyl-4-yl)methyl]animo]benzoate [MBA].

Reference Example 6

Synthesis of tetraethyl orthocarbonate [TEC]

NaOEt (530 kg) was dissolved in ethanol (1810 kg) under a nitrogen atmosphere, and the solution was heated to about 60° C. Chloropicrin (264 kg) was added dropwise over about 2 hours while maintaining at 57 to 64° C. The mixture was cooled to 35 to 45° C., and washed successively with a 15.8% aqueous sodium chloride solution (8670 kg) and a 19.2% aqueous sodium chloride solution (1040 kg). The insolubles were settled by centrifugation, and the solution was distilled under reduced pressure (88° C., 70 mmHg) to give tetraethyl orthocarbonate [TEC](180 kg, 58.3%).

Reference Example 7

Synthesis of methyl 1-[(2'-cyanobiphenyl-4-yl)methyl]-2-ethoxybenzimidazole-7-carboxylate [BEC]

The concentrate of methyl 3-amino-2-N-[(2'-cyanobiphenyl-4-yl)methyl]aminobenzoate [MBA] obtained in Reference Example5, tetraethyl orthocarbonate [TEC] obtained in Reference Example 6 (397 kg) and acetic acid (62 kg) were mixed, and the mixture was heated (78 to 82° C.) under reflux for about 1 to 2 hrs. The reaction solution was cooled, and methanol (1680 L), a 24% aqueous sodium hydroxide solution (65 L) and water (2030 L) were added. The mixture was stirred at 60 to 30° C. for 2 hours, and the pH was adjusted to 5 to 7. After cooled to 5° C. or lower, the precipitated crystals were separated, and washed with cold water (2500 L) and cold ethyl acetate (500 L) to give first crystals. The mother liquor and the washing were concentrated under reduced pressure, followed by cooling to 5° C. or lower, and the precipitated crystals were separated, and washed with cold ethyl acetate (20 L) to give second crystals. The first and second crystals were combined, and dissolved in ethyl acetate (4890 L) under reflux. A seed crystal was added at about 70° C., and cooled to 5° C. The crystals were separated, and washed with cold ethyl acetate (200 L), followed by drying to give methyl 1-[(2'-cyanobiphenyl-4-yl)methyl]-2-ethoxybenzimidazole-7-carboxylate [BEC] (361 kg, 84.8%).

mp. 168.5–169.5° C. $^1$H-NMR(200 MH$_z$, CDCl$_3$) δ: 1.42 (3H,t), 3.71(3H,s), 4.63(2H,q), 5.59(2H,s), 7.09(2H,d), 7.20 (1H,t), 7.45–7.59(5H,m), 7.69–7.80(2H,m), 7.92(1H,dd) IR(KBr) cm$^{-1}$: 2225, 1725, 1550, 1480, 1430, 1280, 1250, 1040, 760, 750

Reference Example 8

Synthesis of Trioctyltin Azide [TOTA]

Sodium azide (160 kg) was dissolved in pure water (505 L), and the solution was cooled to 3 to 10° C. Trioctyltin chloride [TOTC] (847 kg) was added dropwise over 1 to 3 hours, followed by stirring at 5 to 10° C. for about 2 hours. The reaction solution was extracted with methylene chloride (1822 kg, then 546 kg). The methylene chloride layer was washed with a mixture of pure water (50 L) and a 10% aqueous sodium chloride solution (440 L), and the methylene chloride layer was concentrated under reduced pressure to give trioctyltin azide [TOTA].

Reference Example 9

Synthesis of methyl 2-ethoxy-1-[[2'-(1H-tetrazol-5-yl)biphenyl-4-yl]methyl]benzimidazole-7-carboxylate [MET]

The methyl 1-[(2'-cyanobiphenyl-4-yl)methyl]2-ethoxybenzimidazole-7-carboxylate [BEC] (228 kg) obtained in Reference Example 7, the concentrate of trioctyltin azide [TOTA] obtained in Reference Example 8 and toluene (1148 L) were heated (115 to 120° C.) under reflux for about 40 hours. The reaction solution was cooled, and concentrated under reduced pressure. Ethanol (764 kg) and an aqueous sodium nitrite solution (135 kg/460 L) were added to the residue, and the pH was adjusted to 4.5 to 5.5 with concentrated hydrochloric acid (about 224 kg). Ethyl acetate (735 L) was added thereto, and the pH was adjusted to 0.5 to 1.5 with concentrated hydrochloric acid (about 100 L). Hexane (1005 L) was added, and the pH was adjusted to 3.5±0.5 with 4% aqueous sodium hydroxide solution. The solution was cooled to 10° C. or lower, and stirred for 1 hour. The crystals were separated, and washed with a mixture of ethyl acetate (106 L) and hexane (310 L), and then with hexane (410 L) to give wet MET (396.6 kg).

Reference Example 10

Synthesis of 2-ethoxy-1-[[2'-(1H-tetrazol-5-yl)biphenyl-4-yl]methyl]benzimidazole-7-carboxylic acid An aqueous sodium hydroxide solution (73 kg/826 L) was added to the wet MET (369.6 kg) obtained in Reference Example 9, and the mixture was stirred at 68 to 72° C. for 1 to 2 hours. The reaction solution was cooled, and washed twice with methylene chloride (486 kg) and once with toluene (366 L). Methanol (1437 L) was added to the aqueous layer, the pH was adjusted to 7.0±0.5 with concentrated hydrochloric acid (about 35 L). Activated charcoal (11 kg) was added, followed by stirring for about 30 minutes. The activated charcoal was filtered off, and concentrated hydrochloric acid (about 20 L) was added until the solution became cloudy, followed by stirring at 25±5° C. for about 1 hour. Water (487 L) was added, and the pH was adjusted to 3.5±0.3 with concentrated hydrochloric acid (about 85 L). After stirring at 24 to 30° C. for about 30 minutes, water (687 L)

was added, and the mixture was cooled to 10° C. or lower, and stirred for about 1 hour. The crystals were separated, washed with water (412 L) and then acetone (427 L), ground, and dried to give 2-ethoxy-1-[[2'-(1H-tetrazol-5-yl) biphenyl-4-yl]methyl]benzimidazole-7-carboxylic acid (200 kg, 82.0%).

mp. 183–185° C. $^1$NMR (200 MHz, DMSO-d$_6$) δ: 1.38 (3H,t), 4.58(2H,q), 5.63(2H,s), 6.97(4H,q), 7.17(1H,t), 7.47–7.68(6H,m) IR(KBr)cm$^{-1}$:1710, 1550, 1480, 1430, 1280, 1240, 1040, 760

Example 1

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve them. Activated charcoal (0.15 g) was added, and the mixture was stirred for about 30 minutes. Activated charcoal was removed by filtration, and washed with THF-water (THF: water=9:1) (10 mL). Water (87.5 mL) was added dropwise to the filtrate and washing. After stirring for about 1 hour, the crystals were separated, and washed with THF-water (THF:water=2:3) (20 mL). Drying afforded 4.5 g of Compound (I) (yield 90%).

The crystals were analyzed by high performance liquid chromatography (condition(A)) and, as a result, ketone compound was 0.08% and ethyl ester compound was 0.06% as analogues in the crystals.

The crystals were analyzed by gas chromatography and, as a result, THF was 3780 ppm as a residual solvent in the crystals. In addition, other residual solvents were not detected.

The crystals were analyzed by Atomic Absorption Spectrometry and, as a result, the content of Sn in the crystals was below quantitation limit (0.6 ppm).

Example 2

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve them. Activated charcoal (0.15 g) was added, and the mixture was stirred for about 30 minutes. Activated charcoal was removed by filtration, and washed with acetone (20 mL). Acetone (100 mL) was added to the combined filtrate and washing. After stirring for about 20 hours, heptane (100 mL) was added dropwise. After stirring for about 1 hour, the crystals were separated and washed with acetone-heptane (acetone:heptane=1:1) (20 mL). Drying afforded 3.9 g of Compound (I) (yield 78%).

The crystals were analyzed by high performance liquid chromatography (condition(A)) and, as a result, ketone compound was 0.09% and ethyl ester compound was 0.05% as analogues in the crystals.

The crystals were analyzed by gas chromatography and, as a result, THF was 190 ppm, acetone was 340 ppm and heptane was below quantitation limit as a residual solvent in the crystals. In addition, other residual solvents were not detected.

The crystals were analyzed by Atomic Absorption Spectrometry and, as a result, the content of Sn in the crystals was below quantitation limit (0.6 ppm).

Example 3

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with acetone (20 mL) The combined filtrate and washing was passed through Posidyne filter. The Posidyne filter was washed with acetone (20 mL). Acetone (80 mL) was added to the combined filtrate and washing. After stirring for about 20 hours, heptane (100 mL) was added dropwise. After stirring for about 1 hour, the crystals were separated, and washed with acetone-heptane (acetone:heptane=1:1) (20 mL). Drying afforded 3.9 g of Compound (I) (yield 78%).

The crystals were analyzed by high performance liquid chromatography (condition(A)) and, as a result, ketone compound was 0.08% and ethyl ester compound was 0.05% as analogues in the crystals.

The crystals were analyzed by gas chromatography and, as a result, THF was 150 ppm, acetone was 300 ppm and heptane was below quantitation limit as a residual solvent in the crystals. In addition, other residual solvents were not detected.

The crystals were analyzed by Atomic Absorption Spectrometry and, as a result, the content of Sn in the crystals was below quantitation limit (0.6 ppm).

Endotoxin and bacteria in the crystals were investigated, and it was found that endotoxin and bacteria were not present.

Reference Example 11

2-Ethoxy-1-[[2'-(1H-tetrazol-5-yl)biphenyl-4-yl]methyl]-1H-benzimidazole-7-carboxylic acid (350 g, 0.79 mol), ethanol (11.2 L) at about 70° C. and purified water (1.12 L) at 70° C. were mixed and the mixture was stirred at about 75° C. for about 30 minutes. The mixture was gradually cooled to about 10° C. The crystals were separated, and washed with ethanol (580 mL). The resulting wet crystals, ethanol (8.980 L) at about 70° C. and purified water (898 mL) at 70° C. were mixed, and the mixture was dissolved at 75° C. The solution was gradually cooled to about 10° C. The crystals were separated, and washed with ethanol (580 mL). The resulting wet crystals were added to a solution obtained by mixing sodium hydroxide (81.7 g) and purified water (933 mL). The mixture was stirred at about 80° C. for about 2.5 hours. The mixture was cooled to about 10° C., and methanol (1.75 L) was added. Concentrated hydrochloric acid was added dropwise at 10° C. or lower to adjust the pH to about 7.5. Activated charcoal (11.7 g) was added, and the mixture was stirred at the same temperature for about 10 minutes. Activated charcoal was removed by filtration, and washed with purified water (60 mL). Concentrated hydrochloric acid was added dropwise to the combined filtrate and washing at 10° C. or lower, and the pH was adjusted to about 6. Purified water (540 mL) was added, and the solution was stirred at 10° C. or lower for about 1 hour. Concentrated hydrochloric acid was added dropwise at 10° C. or lower, and the pH was adjusted to about 3.5. Purified water (770 mL) was added, and the crystals were separated, and washed with purified water (3 L). The resulting wet crystals were added to a solution obtained by mixing sodium hydroxide (53 g) and purified water (667 mL). After dissolution, purified water (667 mL) was added. The solution was ultrafiltered, and the ultrafilter membrane was washed with purified water (270 mL). Methanol (3.9 L) was added to the combined filtrate and washing. Concentrated hydrochloric acid was added dropwise at 10° C. or lower to adjust the pH to about 3.5. Distilled water (2 L) was added, and the solution was stirred at 10° C. or lower for about 45 minutes. The crystals were separated, and washed successively with distilled water (3.9 L) and acetone (1.2 L) cooled to 10° C. or lower. Drying afforded 230 g of Compound (I) (yield 66%).

The crystals were analyzed by high performance liquid chromatography (condition(A)) and, as a result, ketone compound was 0.3% and ethyl ester compound was 0.1% as analogues in the crystals.

The crystals were analyzed by Atomic Absorption Spectrometry and as a result, the content of Sn in the crystals was below quantitation limit (0.6 ppm).

Reference Example 12

Methyl 2-ethoxy-1-[[2'-(1H-tetrazol-5-yl)biphenyl-4-yl]methyl]-1H-bemzimidazole-7-carboxylate (3 kg, 6.60 mol), acetone (67 L) and purified water (6.7 L) were mixed. Acetone-water (acetone:water=10:1) were added until they were dissolved at 55 to 60° C. Activated charcoal (150 g) was added, and the mixture was stirred at the same temperature for about 10 minutes. Activated charcoal was removed by filtration, and washed with acetone-purified water (acetone:purified water=10:1) (3 L). The solution was gradually cooled to about 10° C., and stirred for about 2 hours. The crystals were separated, and washed with acetone-purified water (acetone:purified water=10:1) (6 L). The resulting wet crystals, acetone (37 L) and purified water (3.7 L) were mixed. Acetone-purified water (acetone:purified water=10:1) were added until they were dissolved at 55 to 60° C. The solution was gradually cooled to about 10° C., and stirred for about 2 hours. The crystals were separated, and washed with acetone-purified water (acetone:purified water=10:1) (10 L). After drying, the resulting crystals were added to a solution obtained by mixing sodium hydroxide (540 g) and purified water (6750 mL). The reaction was allowed to proceed at 65 to 75° C. for about 2 hours. Methanol (1350 mL) was added at 20 to 30° C. Concentrated hydrochloric acid was added dropwise at 0 to 10° C. to adjust the pH to about 7.5. Activated charcoal (94.5 g) was added, and the mixture was stirred at the same temperature for about 30 minutes. Activated charcoal was removed by filtration, followed by washing with methanol-purified water (methanol:purified water=2:1) (2025 mL). Concentrated hydrochloric acid was added dropwise at 0 to 10° C. to adjust the pH to about 3.5. Purified water (11.5 L) was added, and the solution was stirred at 0 to 10° C. for about 45 minutes. The crystals were separated, and washed with purified water (1350 mL). The resulting wet crystals were added to a solution obtained by mixing sodium hydroxide (263.3 g) and purified water (3375 mL). After dissolution, purified water (3375 mL) was added. The solution was ultrafiltered, and the ultrafilter membrane was washed with purified water (1350 mL). Methanol (20.3 L) was added to the combined filtrate and washing. Concentrated hydrochloric acid was added dropwise at 0 to 10° C. to adjust a pH to about 3.5. Distilled water (10.1 L) was added, and the solution was stirred at 0 to 10° C. for about 45 minutes. The crystals were separated, and washed with distilled water (20.3 L). Drying afforded 1215 g of Compound (I) (yield 41.9%).

The crystals were analyzed by high performance liquid chromatography (Condition (A)) and, as a result, ketone compound was 0.22% and ethyl ester compound was 0.06% as analogues in the crystals.

The crystals were analyzed by Atomic Absorption Spectrometry and, as a result, the content of Sn in the crystals was below quantitation limit (0.6 ppm).

Example 4

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with THF-water (THF:water=9:1) (10 mL). Water (87.5 mL) was added dropwise to the combined filtrate and washing. After stirring for about 1 hour, the crystals were separated and washed with THF-water (THF:water=2:3) (20 mL). The resulting wet crystals and water (50 mL) were mixed, and stirred for about 30 minutes. The crystals were separated, and washed with water (20 mL). Drying afforded 4.4 g of Compound (I) (yield 88%).

The crystals were analyzed by high performance liquid chromatography (Condition (A)) and as a result, ketone compound was 0.12% and ethyl ester compound was 0.13% as analogues in the crystals.

The crystals were analyzed by Atomic Absorption Spectrometry, and as a result, the content of Sn in the crystals was below quantitation limit (0.6 ppm).

Example 5

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with THF-water (THF:water=9:1) (10 mL). Water (87.5 mL) was added dropwise to the combined filtrate and washing. After stirring for about 1 hour, the crystals were separated, and washed with THF-water (THF:water=2:3) (20 mL). The resulting wet crystals and ethanol (50 mL) were mixed, and stirred for about 30 minutes. The crystals were separated, and washed with ethanol (20 mL). Drying afforded 4.0 g of Compound (I) (yield 80%).

The crystals were analyzed by high performance liquid chromatography (condition(A)) and, as a result, ketone compound was 0.12% and ethyl ester compound was 0.11% as analogues in the crystals.

The crystals were analyzed by Atomic Absorption Spectrometry and, as a result, the content of Sn in crystals was below quantitation limit (0.6 ppm).

Example 6

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with THF-water (THF:water=9:1) (10 mL). Water (87.5 mL) was added dropwise to the combined filtrate and washing. After stirring for about 1 hour, the crystals were separated, and washed with THF-water (THF:water=2:3) (20 mL). The resulting wet crystals and acetone (50 mL) were mixed, and stirred for about 30 minutes. The crystals were separated, and washed with acetone (20 mL). Drying afforded 4.0 g of Compound (I) (yield 80%).

The crystals were analyzed by high performance liquid chromatography (Condition (A)) and, as a result, ketone compound was 0.11% and ethyl ester compound was 0.12% as analogues in crystals.

The crystals were analyzed by Atomic Absorption Spectrometry and, as a result, the content of Sn in the crystals was below quantitation limit (0.6 ppm).

Example 7

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with THF-water (THF:water=9:1) (10 mL). Water (87.5 mL) was added dropwise to the combined filtrate and washing. After stirring for about 1 hour, the crystals were separated, and washed with THF-water (THF:water=2:3) (20 mL). The resulting wet crystals and ethyl acetate (50 mL) were mixed, and stirred for about 30 minutes. The crystals were separated, and washed with ethyl acetate (20 mL). Drying afforded 4.0 g of Compound (I) (yield 80%).

The crystals were analyzed by high performance liquid chromatography (condition(A)) and, as a result, ketone compound was 0.11% and ethyl ester compound was 0.12% as analogues in the crystals.

The crystals were analyzed by Atomic Absorption Spectrometry and, as a result, the content of Sn in the crystals was below quantitation limit (0.6 ppm).

Example 8

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with THF-water (THF:water=9:1) (10 mL). Water (87.5 mL) was added dropwise to the combined filtrate and washing over about 10 minutes. After stirring for about 1 hour, the crystals were separated, and washed with THF-water (THF:water=2:3) (20 mL). Drying afforded 4.2 g of Compound (I) (yield 84%).

The crystals were analyzed by high performance liquid chromatography (condition(A)), as a result, ketone compound was 0.05% and ethyl ester compound was 0.13% as analogues in the crystals.

The crystals were analyzed by Atomic Absorption Spectrometry and, as a result, the content of Sn in the crystals was below quantitation limit (0.6 ppm).

Example 9

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with THF-water (THF:water=9:1) (10 mL). The combined filtrate and washing was added dropwise to water (87.5 mL). After stirring for about 1 hour, the crystals were separated, and washed with THF-water (THF:water=2:3) (20 mL). Drying afforded 4.4 g of Compound (I) (yield 88%).

The crystals were analyzed by high performance liquid chromatography (condition(A)) and, as a result, ketone compound was 0.23% and ethyl ester compound was 0.13% as analogues in the crystals.

The crystals were analyzed by Atomic Absorption Spectrometry and, as a result, the content of Sn in the crystals was below quantitation limit (0.6 ppm).

Example 10

2-(Ethoxy-1-[[2'-(1H-tetrazol-5-yl)biphenyl-4-yl]methyl]-1H-benzimidazole-7-carboxylic acid (5.0 g, 0.011 mol), DMSO (7 mL) and acetone (63 mL) were mixed to dissolve. Activated charcoal (0.15 g) was added, and the mixture was stirred for about 30 minutes. Activated charcoal was removed by filtration, and washed with DMSO-acetone (DMSO:acetone=9:1) (10 mL). Water (80 mL) was added dropwise to the combined filtrate and washing. After stirring for about 1 hour, the crystals were separated, and washed with acetone-water (acetone:water=1:1) (20 mL). Drying afforded 4.5 g of Compound (I) (yield 90%).

The crystals were analyzed by high performance liquid chromatography (condition(A)) and, as a result, ketone compound was 0.29% and ethyl ester compound was 0.10% as analogues in the crystals.

The crystals were analyzed by Atomic Absorption Spectrometry and, as a result, the content of Sn in the crystals was below quantitation limit (0.6 ppm).

Example 11

2-Ethoxy-1-[[2'-(1H-tetrazol-5-yl)biphenyl-4-yl]methyl]-1H-benzimidazole-7-carboxylic acid (5.0 g, 0.011 mol), DMSO (7 mL) and acetone (63 mL) were mixed to dissolve. Activated charcoal (0.15 g) was added, and the mixture was stirred for about 30 minutes. Activated charcoal was removed by filtration, and washed with DMSO-acetone (DMSO:acetone=9:1) (10 mL). Water (34 mL) was added dropwise to the combined filtrate and washing. After stirring for about 1 hour, the crystals were separated, and washed with acetone-water (acetone:water=1:1) (20 mL). Drying afforded 4.0 g of Compound (I) (yield 80%).

The crystals were analyzed by high performance liquid chromatography (condition(A)) and, as a result, ketone compound was 0.25% and ethyl ester compound was 0.11% as analogues in the crystals.

The crystals were analyzed by Atomic Absorption Spectrometry and, as a result, the content of Sn in the crystals was below quantitation limit (0.6 ppm).

Example 12

2-Ethoxy-1-[[2'-(1H-tetrazol-5-yl)biphenyl-4-yl]methyl]-1H-benzimidazole-7-carboxylic acid (5.0 g, 0.011 mol), THF (63 mL), acetone (63 mL) and water (14 mL) were mixed to dissolve. Activated charcoal (0.15 g) was added, and the mixture was stirred for about 30 minutes. Activated charcoal was removed by filtration, and washed with THF-acetone (THF:acetone=1:1) (10 mL). Water (70 mL) was added dropwise to the combined filtrate and washing. After stirring for about 1 hour, crystals were separated, and washed with acetone-water (acetone:water=1:1 ) (20 mL). Drying afforded 3.0 g of Compound (I) (yield 60%).

The crystals were analyzed by high performance liquid chromatography (condition(A)) and, as a result, ketone compound was 0.06% and ethyl ester compound was 0.09% as analogues in crystals.

The crystals were analyzed by gas chromatography and, as a result, THF was 940 ppm and acetone was 460 ppm as a residual solvent in the crystals. Other residual solvents were not detected.

The crystals were analyzed by Atomic Absorption Spectrometry and, as a result, the content of Sn in the crystals was below quantitation limit (0.6 ppm).

Example 13

2-Ethoxy-1-[[2'-(1H-tetrazol-5-yl)biphenyl-4-yl]methyl]-1H-benzimidazole-7-carboxylic acid (5.0 g, 0.011 mol), THF (90 mL), ethanol (90 mL) and water (20 mL) were mixed to dissolve. Activated charcoal (0.15 g) was added, and the mixture was stirred for about 30 minutes. Activated charcoal was removed by filtration, and washed with THF-ethanol-(THF:ethanol=1:1) (10 mL). Water (100 mL) was added dropwise to the combined filtrate and washing. After stirring for about 1 hour, the crystals were separated, and washed with ethanol-water (ethanol:water=1:1) (20 mL). Drying afforded 3.3 g of Compound (I) (yield 66%).

The crystals were analyzed by high performance liquid chromatography (condition(A)) and, as a result, ketone compound was 0.04% and ethyl ester compound was 0.07% as analogues in the crystals.

The crystals were analyzed by gas chromatography and, as a result, THF was 1000 ppm and ethanol was 570 ppm as a residual solvent in the crystals. Other residual solvents were not detected.

The crystals were analyzed by Atomic Absorption Spectrometry and, as a result, the content of Sn in the crystals was below quantitation limit (0.6 ppm).

Example 14

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with ethanol (10 mL). Ethanol (98 mL) was added to the combined filtrate and washing, and water (102 mL) was added dropwise. After stirring for about 1 hour, the crystals were separated, and washed with ethanol-water (ethanol:water=1:1) (20 mL). Drying afforded 3.8 g of Compound (I) (yield 76%).

The crystals were analyzed by high performance liquid chromatography (condition(A)) and, as a result, ketone compound was 0.17% and ethyl ester compound was 0.10% as analogues in the crystals.

The crystals were analyzed by gas chromatography and, as a result, THF was 1330 ppm and ethanol was 460 ppm as a residual solvent in the crystals. Other residual solvents were not detected.

The crystals were analyzed by Atomic Absorption Spectrometry and, as a result, the content of Sn in the crystals was below quantitation limit (0.6 ppm).

Example 15

2-Ethoxy-1-[[2'-(1H-tetrazol-5-yl)biphenyl-4-yl]methyl]-1H-benzimidazole-7-carboxylic acid (5.0 g, 0.011 mol) and DMSO (20 mL) were mixed to dissolve. Activated charcoal (0.15 g) was added, and the mixture was stirred for about 30 minutes. Activated charcoal was removed by filtration, and washed with acetone-THF (acetone:THF=5:1) (10 mL). Acetone-THF (acetone:THF=5:1) (60 mL) were added to the combined filtrate and washing, and water (60 mL) was added dropwise. After stirring for about 1 hour, the crystals were separated, and washed with acetone-water (acetone:water=1:1) (20 mL). Drying afforded 4.4 g of Compound (I) (yield 88%).

The crystals were analyzed by high performance liquid chromatography (condition(A)) and, as a result, ketone compound was 0.16% and an ethyl ester compound was 0.15% as analogues in the crystals.

The crystals were analyzed by Atomic Absorption Spectrometry and, as a result, the content of Sn in the crystals was below quantitation limit (0.6 ppm).

Example 16

2-Ethoxy-1-[[2'-(1H-tetrazol-5-yl)biphenyl-4-yl]methyl]-1H-benzimidazole-7-carboxylic acid (5.0 g, 0.011 mol) and DMSO (20 mL) were mixed to dissolve. Activated charcoal (0.15 g) was added, and the mixture was stirred for about 30 minutes. Activated charcoal was removed by filtration, and washed with ethanol-THF (ethanol:THF=5:1)(10 mL). Ethanol-THF (ethanol:THF=5:1) (60 mL) was added to the combined filtrate and washing, and water (60 mL) was added dropwise. After stirring for about 1 hour, the crystals were separated, and washed with ethanol-water (ethanol:water=1:1) (20 mL). Drying afforded 4.4 g of Compound (I) (yield 88%).

The crystals were analyzed by high performance liquid chromatography (condition(A)) and, as a result, ketone compound was 0.19% and ethyl ester compound was 0.11% as analogues in crystals.

The crystals were analyzed by Atomic Absorption Spectrometry and, as a result, the content of Sn in the crystals was below quantitation limit (0.6 ppm).

Example 17

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with acetone (10 mL). Acetone (98 mL) was added dropwise to the combined filtrate and washing. After stirring for about 3 hours, the crystals were separated, and washed with acetone (20 mL) Drying afforded 1.7 g of Compound (I) (yield 34%).

The crystals were analyzed by high performance liquid chromatography (condition(A)) and, as a result, ketone compound was 0.05% and ethyl ester compound was 0.06% as analogues in the crystals.

The crystals were analyzed by gas chromatography and, as a result, THF was 160 ppm and acetone was 110 ppm as residual solvent in the crystals. Other residual solvents were not detected.

The crystals were analyzed by Atomic Absorption Spectrometry and, as a result, the content of Sn in the crystals was below quantitation limit (0.6 ppm).

Example 18

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with acetone (10 mL). Acetone (98 mL) was added dropwise to the combined filtrate and washing. After stirring for about 20 hours, the solution was stirred at −15 to −20° C. for about 3 hours. The crystals were separated, and washed with acetone (20 mL). Drying afforded 2.5 g of Compound (I) (yield 50%).

The crystals were analyzed by high performance liquid chromatography (condition(A)) and, as a result, ketone compound was 0.08% and ethyl ester compound was 0.06% as analogues in the crystals.

The crystals were analyzed by gas chromatography and, as a result, THF was 220 ppm and acetone was 230 ppm as residual solvent in the crystals. Other residual solvents were not detected.

The crystals were analyzed by Atomic Absorption Spectrometry and, as a result, the content of Sn in the crystals was below quantitation limitation (0.6 ppm).

Example 19

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with acetone (20 mL). Acetone (100 mL) was added to the combined filtrate and washing. After stirring for about 2 hours, heptane (100 mL) was added dropwise. After stirring for about 1 hour, the crystals were separated, and washed with acetone-heptane (acetone:heptane=1:1) (20 mL). Drying afforded 3.8 g of Compound (I) (yield 76%).

The crystals were analyzed by high performance liquid chromatography (condition(A)) and, as a result, ketone compound was 0.24% and ethyl ester compound was 0.05% as analogues in crystals.

The crystals were analyzed by Atomic Absorption Spectrometry and, as a result, the content of Sn in the crystals was below quantitation limit (0.6 ppm).

Example 20

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with acetone (20 mL). Acetone (100 mL) was added to the combined filtrate and washing. After stirring for about 2 hours, tert-butyl methyl ether (100 mL) was added dropwise. After stirring for about 1 hour, the crystals were separated, and washed with acetone-tert-butyl methyl ether (acetone:tert-butyl methyl ether=1:1) (20 mL). Drying afforded 2.9 g of Compound (I) (yield 58%).

The crystals were analyzed by high performance liquid chromatography (condition(A)) and, as a result, ketone compound was 0.10% and ethyl ester compound was 0.05% as analogues in the crystals.

The crystals were analyzed by gas chromatography and, as a result, THF was 590 ppm, acetone was 440 ppm and tert-butyl methyl ether was 180 ppm as a residual solvent in the crystals. Other residual solvents were not detected.

The crystals were analyzed by Atomic Absorption Spectrometry and, as a result, the content of Sn in the crystals was below quantitation limit (0.6 ppm).

Example 21

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with acetone (20 mL). Acetone (100 mL) was added to the combined filtrate and washing. After stirring for about 20 hours, tert-butyl methyl ether (100 mL) was added dropwise. After stirring for about 1 hour, the crystals were separated, and washed with acetone-tert-butyl methyl ether (acetone:tert-butyl methyl ether=1:1) (20 mL). Drying afforded 2.9 g of Compound (I) (yield 58%).

The crystals were analyzed by high performance liquid chromatography (condition(A)) and, as a result, ketone compound was 0.06% and ethyl ester compound was 0.06% as analogues in the crystals.

The crystals were analyzed by gas chromatography and, as a result, THF was 120 ppm, acetone was 200 ppm and tert-butyl methyl ether was below quantitation limit as a residual solvent in the crystals. Other residual solvents were not detected.

The crystals were analyzed by Atomic Absorption Spectrometry and, as a result, the content of Sn in the crystals was below quantitation limit (0.6 ppm).

Example 22

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with tert-butyl methyl ether (20 mL). tert-Butyl methyl ether (100 mL) was added to the combined filtrate and washing. After stirring for about 20 hours, the crystals were separated, and washed with tert-butyl methyl ether (20 mL). Drying afforded 4.1 g of Compound (I) (yield 82%).

The crystals were analyzed by high performance liquid chromatography (condition(A)) and, as a result, ketone compound was 0.08% and ethyl ester compound was 0.10% as analogues in the crystals.

The crystals were analyzed by gas chromatography, as a result, THF was 2340 ppm and tert-butyl methyl ether was 990 ppm as a residual solvent in the crystals. Other residual solvents were not detected.

The crystals were analyzed by Atomic Absorption Spectrometry and, as a result, the content of Sn in the crystals was below quantitation limit (0.6 ppm).

Example 23

2-Ethoxy-1-[[2'-(1H-tetrazol-5-yl)biphenyl-4-yl]methyl]-1H-benzimidazole-7-carboxylic acid (5.0 g, 0.011 mol,), THF (54 mL) and water (6 mL) were mixed to dissolve. Activated charcoal (0.15 g) was added, and the mixture was stirred for about 30 minutes. Activated charcoal was removed by filtration, and washed with tert-butyl methyl ether (20 mL). tert-Butyl methyl ether (20 mL) was added to the combined filtrate and washing. After stirring for about 20 hours, tert-butyl methyl ether (80 mL) was added dropwise. After stirring for about 1 hour, the crystals were separated, and washed with tert-butyl methyl ether (20 mL). Drying afforded 3.6 g of Compound (I) (72%).

Example 24

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with heptane (20 mL). Heptane (20 mL) was added to the combined filtrate and washing. After stirring for about 20 hours, heptane (80 mL) was added dropwise. After stirring for about 1 hour, the crystals were separated, and washed with heptane (20 mL). Drying afforded 4.0 g of Compound (I) (80%).

Example 25

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with methanol (20 mL). Methanol (40 mL) was added to the combined filtrate and washing. After stirring for about 20 hours, the crystals were separated, and washed with methanol (20 mL). Drying afforded 3.8 g of Compound (I) (76%).

Example 26

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with ethyl acetate (20 mL). Ethyl acetate (40 mL) was added to the combined filtrate and washing. After stirring for about 20 hours, the crystals were separated, and washed with ethyl acetate (20 mL). Drying afforded 3.2 g of Compound (I) (64%).

Example 27

2-(Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with ethyl acetate (20 mL). The combined filtrate and washing was passed through Posidyne filter. The Posidyne filter was washed with ethyl acetate (20 mL). Ethyl acetate (20 mL) was added to the combined filtrate and washing. After stirring for about 20 hours, the crystals were separated, and washed with ethyl acetate (20 mL). Drying afforded 3.6 g of Compound (I) (72%).

Example 28

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with 1-propanol (20 mL). 1-Propanol (100 mL) was added to the combined filtrate and washing. After stirring for about 20 hours, the crystals were separated and washed with 1-propanol (20 mL). Drying afforded 3.8 g of Compound (I) (76%).

Example 29

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with 2-propanol (20 mL). 2-Propanol (40 mL) was added to the combined filtrate and washing. After stirring for about 20 hours, the crystals were separated, and washed with 2-propanol (20 mL). Drying afforded 3.2 g of Compound (I) (64%).

Example 30

2-Ethoxy-1-[[2'-(1H-tetrazol-5-yl)biphenyl-4-yl]methyl]-1H-benzimidazole-7-carboxylic acid (5.0 g, 0.011 mol), THF (54 mL) and water (6 mL) were mixed to dissolve. Activated charcoal (0.15 g) was added, and the mixture was stirred for about 30 minutes. Activated charcoal was removed by filtration, and washed with ethyl acetate (20 ML). Ethyl acetate (40 mL) was added to the combined filtrate and washing. After stirring for about 20 hours, heptane (60 mL) was added dropwise. After stirring for about 1 hour, the crystals were separated, and washed with ethyl acetate-heptane (ethyl acetate:heptane=1:1 (20 mL). Drying afforded 4.0 g of Compound (I) (80%).

Example 31

2-Ethoxy-1-[[2'-(1H-tetrazol-5-yl)biphenyl-4-yl]methyl]-1H-benzimidazole-7-carboxylic acid (5.0 g) (0.011 mol), THF (54 mL) and water (6 mL) were mixed to dissolve. Activated charcoal (0.15 g) was added, and the mixture was stirred for about 30 minutes. Activated charcoal was removed by filtration, and washed with ethyl acetate (20 mL). The combined filtrate and washing was passed through Posidyne filter. The Posidyne filter was washed with ethyl acetate (20 mL). Ethyl acetate (20 mL) was added to the combined filtrate and washing. After stirring for about 20 hours, heptane (60 mL) was added dropwise. After stirring for about 1 hour, the crystals were separated, and washed with ethyl acetate-heptane (ethyl acetate:heptane=1:1) (20 mL). Drying afforded 4.0 g of Compound (I) (80%).

Example 32

2-Ethoxy-1-[[2'-(1H-tetrazol-5-yl)biphenyl-4-yl]methyl]-1H-benzimidazole-7-carboxylic acid (5.0 g, 0.011 mol) was dissolved in 1N sodium hydroxide (24 mL, 0.024 mol). The solution was ultrafiltered. Methanol (50 mL) was added to the filtrate, and concentrated hydrochloric acid was added thereto under ice-cooling to adjust the pH to about 3. The crystals were collected by filtration, and washed with water (100 mL). THF (54 mL) was added to the crystals, and dissolved them. Activated charcoal (0.15 g) was added, and the mixture was stirred for about 30 minutes. Activated charcoal was removed by filtration, and washed with acetone (20 mL). Acetone (100 mL) was added to the combined filtrate and washing. After stirring for about 20 hours, heptane (100 mL) was added dropwise. After stirring for about 1 hour, the crystals were separated, and washed with acetone-heptane (acetone:heptane=1:1) (20 mL) Drying afforded 4.0 g of Compound (I) (yield 80%).

The crystals were analyzed by high performance liquid chromatography (condition(A)) and, as a result, ketone compound was 0.07% and ethyl ester compound was 0.04% as analogues in the crystals.

The crystals were analyzed by gas chromatography and, as a result, THF was 170 ppm, acetone was 320 ppm and heptane was below quantitation limit as a residual solvent in the crystals. Other residual solvents were not detected.

The crystals were analyzed by Atomic Absorption Spectrometry and, as a result, the content of Sn in the crystals was below quantitation limit (0.6 ppm).

Endotoxin in the crystals was investigated, and it was found that endotoxin was not present.

INDUSTRIAL APPLICABILITY

According to the process of the present invention, contaminants which are contained in Compound (I) or a salt thereof and are difficult to remove, such as tin compounds, analogues of Compound (I) (e.g. ketone compounds and ethyl ester compounds) and residual organic solvents (e.g. dichloromethane) can be easily removed, and the crystal of Compound (I) or a salt thereof can be produced with high yield and convenient procedure, effectively and on an industrial large-scale.

The invention claimed is:

1. A process for producing a crystal of 2-ethoxy-1-[[2'-(1H-tetrazol-5-yl)biphenyl-4-yl]methyl]-1H-benzimidazole-7-carboxylic acid, which comprises crystallizing from a solution or suspension containing 2-ethoxy-1-[[2'-(1H-tetrazol5-yl) biphenyl-4-yl]methyl]-1H-benzimidazole-7-carboxylic acid or a salt thereof and an aprotic polar solvent, wherein the aprotic polar solvent is tetrahydrofuran, dimethylformamide, dimethyl sulfoxide, hexamethylphosphoric triamide, or a mixed solvent of two or more of them.

2. A process for producing a crystal of 2-ethoxy-1-[[2'-(1H-tetrazol-5-yl) biphenyl-4-yl]methyl]-1H-benzimidazole-7-carboxylic acid, which comprises crystallizing from a solution containing 2-ethoxy-1-[[2'-(1H-tetrazol-5-yl)biphenyl-4-yl]methyl]-1H-benzimidazole-7-carboxylic acid and an aprotic polar solvent, wherein the aprotic polar solvent is tetrahydrofuran, dimethylformamide, dimethyl sulfoxide, hexamethylphosphoric triamide, or a mixed solvent of two or more of them.

3. The process according to claim 1 wherein the aprotic polar solvent is one or more kinds of solvents selected from tetrahydrofuran, dimethylformamide, dimethyl sulfoxide and hexamethylphosphoric triamide.

4. The process according to claim 1 wherein the aprotic polar solvent is tetrahydrofuran.

5. The process according to claim 1 which comprises crystallizing at about 0 to about 30° C.

6. The process according to claim 1 wherein a step in which a crystallized crystal is dissolved or suspended in a solvent containing an aprotic polar solvent, followed by being crystallized, is repeated one or more times.

7. The process according to claim 2 wherein the aprotic polar solvent is one or more kinds of solvents selected from tetrahydrofuran, dimethylformamide, dimethyl sulfoxide and hexamethylphosphoric triamide.

8. The process according to claim 2 wherein the aprotic polar solvent is tetrahydrofuran.

9. The process according to claim 2 which comprises crystallizing at about 0 to about 30° C.

10. The process according to claim 2 wherein a step in which a crystallized crystal is dissolved or suspended in a solvent containing an aprotic polar solvent, followed by being crystallized, is repeated one or more times.

* * * * *

UNITED STATES PATENT AND TRADEMARK OFFICE
CERTIFICATE OF CORRECTION

PATENT NO. : 7,067,546 B2
APPLICATION NO. : 10/485593
DATED : June 27, 2006
INVENTOR(S) : Hideo Hashimoto and Hideaki Maruyama It is certified that error appears in the above-identified patent and that said Letters Patent is hereby corrected as shown below:

Please add on the front page of the patent (73) in the Applicant's name,

--TAKEDA PHARMACEUTICAL COMPANY LIMITED--

Signed and Sealed this

Fourteenth Day of November, 2006

JON W. DUDAS
*Director of the United States Patent and Trademark Office*